United States Patent
Medvedev et al.

(10) Patent No.: US 12,203,126 B2
(45) Date of Patent: Jan. 21, 2025

(54) SYSTEM AND METHOD FOR CLARIFYING A CELL CULTURE HARVEST SOLUTION

(71) Applicant: EXOTHERA S.A., Nivelles (BE)

(72) Inventors: Vasily Medvedev, Nivelles (BE); Tiago Albano, Grimbergen (BE); José Castillo, Brussels (BE)

(73) Assignee: EXOTHERA S.A., Nivelles (BE)

(*) Notice: Subject to any disclaimer, the term of this patent is extended or adjusted under 35 U.S.C. 154(b) by 912 days.

(21) Appl. No.: 17/054,578

(22) PCT Filed: May 13, 2019

(86) PCT No.: PCT/EP2019/062227
§ 371 (c)(1),
(2) Date: Nov. 11, 2020

(87) PCT Pub. No.: WO2019/215344
PCT Pub. Date: Nov. 14, 2019

(65) Prior Publication Data
US 2021/0189454 A1    Jun. 24, 2021

Related U.S. Application Data

(60) Provisional application No. 62/827,009, filed on Mar. 30, 2019, provisional application No. 62/670,220, filed on May 11, 2018.

(51) Int. Cl.
*C12M 3/00* (2006.01)
*C12M 1/00* (2006.01)
*C12Q 1/24* (2006.01)

(52) U.S. Cl.
CPC .............. *C12Q 1/24* (2013.01); *C12M 29/04* (2013.01); *C12M 29/14* (2013.01); *C12M 47/02* (2013.01); *C12M 47/10* (2013.01)

(58) Field of Classification Search
CPC ....... C12M 47/10; C12M 47/04; C12M 47/02; B01L 1/52
See application file for complete search history.

(56) References Cited

U.S. PATENT DOCUMENTS 11,485,947 B2 * 11/2022 Ali .................... C12M 23/26
11,840,684 B2 * 12/2023 Larsen ............... B01D 61/147
(Continued)

FOREIGN PATENT DOCUMENTS

| CN | 102140491 A | 8/2011 |
| WO | 2016185221 A1 | 11/2016 |
| WO | 2018178376 A1 | 10/2018 |

OTHER PUBLICATIONS

Filtrox: Filtrodisc (TM) Bio SD. Single use clarification in a new dimension. Disposable high performance microfiltration system easy scalable from lab to process.; Nov. 1, 2017.
(Continued)

*Primary Examiner* — Nathan A Bowers
(74) *Attorney, Agent, or Firm* — Dickinson Wright PLLC

(57) ABSTRACT

A system for clarifying a cell culture harvest solution, including target molecules and dynamic filter media. A filtration vessel includes a flexible liner and at least one filter having a surface on which the dynamic filter media accumulates into a cake. The cake and filter during filtration operation permit a filtrate including target molecules to pass therethrough while preventing unwanted solid materials from passing therethrough. A backflush source includes a backflush fluid and is fluidly connected to the filtration vessel via the at least one filter. The backflush source, during backflush operation, is adapted to supply backflush fluid back through the at least one filter for removing the cake formed on the filter. Related systems and methods are also disclosed.

17 Claims, 18 Drawing Sheets

(56) References Cited

U.S. PATENT DOCUMENTS

| | | | |
|---|---|---|---|
| 11,890,557 B2* | 2/2024 | Rhodes | C12M 23/28 |
| 2009/0215022 A1* | 8/2009 | Page | C12M 23/44 |
| | | | 435/286.5 |
| 2012/0238011 A1 | 9/2012 | Tuohey et al. | |
| 2016/0348061 A1* | 12/2016 | Diel | C12M 37/02 |
| 2019/0316173 A1* | 10/2019 | Klintstedt | C12N 1/20 |
| 2020/0056144 A1* | 2/2020 | Castillo | C12M 41/40 |
| 2021/0140858 A1* | 5/2021 | Nishioka | C12Q 1/12 |

OTHER PUBLICATIONS

Anonymous: Filtrodisc (TM) Bio SD. Single use clarification in a new dimension. Disposable high performance microfiltration system easy scalable from lab to process.; Dec. 12, 2016.

Anonymous: Filtrox: Single-use clarification of fermentation broths, Internet Citation; Nov. 17, 2016.

Filtrox, Filtrodisc™M, Bio SD, Filtrox AG · Moosmühlestr. 6 · CH-9001 St.Gallen / Switzerland, 4 pages, www.filtrox.ch.

\* cited by examiner

SYSTEM AND METHOD FOR CLARIFYING A CELL CULTURE HARVEST SOLUTION

This application claims the benefit of U.S. Provisional Patent Application Ser. Nos. 62/670,220 and 62/827,009, the disclosures of which are incorporated herein by reference.

TECHNICAL FIELD

This document relates generally to the field of purification, particularly, cell culturing and biologic manufacturing and, more particularly, to a system and method for clarifying a cell culture harvest solution.

BACKGROUND

In the biologics manufacturing field, there is a need for equipment which has a limited footprint so that it can form part of a "microfacility." Such a microfacility would permit speedy and efficient substitution of components operated under isolators between batch operations. Single-use technology would allow such substitution and prevent the need for costly cleaning and revalidation as well. Thus, the microfacility would offer high yield at higher speed of setup and functionality at substantially lower cost.

Past proposals for clarifying cell cultures as part of the biologics manufacturing process exist, including the disclosure in International Application No. PCT/EP2018/058366, the disclosure of which is incorporated herein by reference. This approach represents an improvement over past approaches by providing a system and method for clarifying a cell culture harvest in an easy, reliable, and inexpensive manner. However, creating and using a "horizontal" cake filter positioned upon an associated filter support at the bottom of the container presents a challenge if any "regeneration" of the filter cake is desired in an easy and efficient manner. This is because the direction of fluid flow through the filter surface is aligned with the direction of gravity.

Because the cake is also not easily removed from the filtration vessel, the size of that vessel must be large enough to accommodate a finite amount of the material (e.g., diatomaceous earth) forming the filter cake. When the vessel is filled beyond a certain point, further introduction of solution is not permitted and the filtration vessel must be emptied or cleaned in order to reuse it. This can impact processing time and cost, since the ratio of the area of filtration to the volume of production of filtrate is low.

It is also known to filter a chemical solution mixed with a dynamic filtration media using a system having a large, rigid vessel with a so-called "candle" filter. In a typical arrangement, the solution is filtered through the candle filter such that a filter cake forms on the surface of the candle filter. The filter cake may be discharged once the operation is complete, and the vessel must be cleaned and revalidated before it can be reused. Thus, the vessel is usually costly and does not permit easy use and operation in a limited space.

Accordingly, a need is identified for a system and method for clarifying a cell culture harvest solution that provides further efficiencies in certain manufacturing environments. Toward this end, the system and method in some embodiments would include one or more small volume vessels, including a disposable filtration vessel that includes one or more candle filters. The system could thus be readily applied as part of a "microfacility" for clarifying the cell culture harvest solution, and then simply disposed of once processing is complete. In one particularly advantageous example, the clarifying system and method would also use the filtrate as a source of a backflush fluid to discharge the filter cake from the candle filter, thereby increasing efficiency and avoiding the need for the introduction of a separate backflush fluid into a sterile environment and eliminating the corresponding costs/challenges.

SUMMARY

According to a first aspect of the disclosure, a system for clarifying a cell culture harvest solution, including target molecules and dynamic filter media is provided. The system comprises a filtration vessel comprising a flexible liner, the filtration vessel including at least one filter having a surface on which the dynamic filter media accumulates into a cake, said cake and at least one filter adapted, during filtration operation, to permit a filtrate including target molecules to pass therethrough and said cake, during filtration operation, adapted to prevent unwanted solid materials from passing therethrough; and a backflush source including a backflush fluid and fluidly connected to the filtration vessel via the at least one filter, said backflush source, during backflush operation, adapted to supply backflush fluid back through the at least one filter for removing the cake formed on the filter.

In some embodiments, the backflush source is a backflush vessel adapted for receiving a portion of the filtrate from the filtration vessel. In some embodiments, the system further includes a bioreactor vessel or intermediate vessel within which the cell culture harvest solution and dynamic filter media is mixed and capable of supplying the cell culture harvest solution to the filtration vessel. In some embodiments, the system further includes a source of dynamic filter media for being combined with the cell culture harvest solution after delivery from a bioreactor or intermediate vessel. In some embodiments, a bioreactor vessel is provided for supplying the cell culture harvest solution to the filtration vessel and an auxiliary vessel is provided for supplying the dynamic filtration media.

In some embodiments, an actuator is provided for causing the flexible liner to collapse and cause liquid therein to pass through the at least one filter. The actuator may comprise a source of pressurized fluid. In some embodiments, the at least one filter is suspended within the filtration vessel. In some embodiments, a waste collector in communication with the filtration vessel is provided for receiving waste therefrom. In some embodiments, a source of buffer is provided in communication with the filtration vessel. In some embodiments, a pump is provided for pumping liquid to the filtration vessel. In some embodiments, a plurality of (candle) filters are in the filtration vessel.

In some embodiments, the backflush source includes a flexible liner, and the system further includes an actuator for causing the flexible liner to collapse and cause fluid therein to pass through the at least one filter and into the filtration vessel. In some embodiments, the filtration vessel further includes a valve for selectively allowing for the draining of fluid therefrom. In some embodiments, the valve is located adjacent to a bottom portion of the vessel.

A further aspect of the disclosure pertains to a method for clarifying a cell culture harvest solution including target molecules and a dynamic filter media into a filtrate including the target molecules. The method comprises delivering the cell culture harvest solution to a filtration vessel including at least one filter adapted for allowing a filtrate but not the dynamic filter media to pass therethrough, the filter having a surface with a surface area, and driving a first liquid flow through the filter to allow a cake to form on the filter and the filtrate to result from passing through the cake; and backflushing the at least one filter.

In some embodiments, the backflushing step comprises passing a liquid through the filter to discharge the cake from the filter. In some embodiments, the method comprises compressing the filtration vessel prior to the backflushing step. In some embodiments, the method includes the step of delivering filtrate to a collector after the backflushing step. In some embodiments, the method comprises the step of compressing the filtration vessel after the backflushing step. In some embodiments, the method comprises the step of introducing a buffer to the filtration vessel after the backflushing step. In some embodiments, the method further includes the step of discharging waste from the filtration vessel after the backflushing step. In some embodiments, the method further includes the step of driving a second liquid flow through the at least one filter to allow another cake to form on the surface of the filter. In some embodiments, the method further includes the step of opening a valve to drain the filtration vessel. In some embodiments, the method further includes the step of combining the cell culture harvest solution after discharge from a bioreactor or intermediate vessel with the dynamic filter media.

According to a further aspect of the disclosure, a method for clarifying a cell culture harvest solution including target molecules and a dynamic filter media into a filtrate including the target molecules but excluding certain impurities is provided. The method comprises delivering a cell culture harvest solution to a filtration vessel including a compressible liner and at least one filter adapted for allowing a filtrate but not the dynamic filter media to pass therethrough, the filter having a surface with a surface area, such that a cake of the dynamic filter media forms on the filter; and compressing the liner to cause liquid within the liner to flow through the filter to create a filtrate.

In some embodiments, the method includes the step of backflushing the at least one filter with the liquid. In some embodiments, the backflushing step comprises backflushing the filter with the filtrate. The step of backflushing the at least one filter with the liquid may comprise backflushing the filter with liquid from a backflush vessel in communication with the filtration vessel.

The method may further comprise passing liquid from the filtration vessel through the filter after the backflushing step. In some embodiments, the compressing step is completed after the delivering step, but before the backflushing step. In some embodiments, the compressing step is completed after the backflushing step.

This disclosure also pertains to an apparatus for clarifying a cell culture harvest solution, including target molecules and dynamic filter media. The apparatus comprises a filtration vessel including at least one candle filter having a surface on which the dynamic filter media accumulates into a cake, said cake and at least one filter adapted, during normal operation, to permit a filtrate including target molecules to pass therethrough and said cake, during normal operation, adapted to prevent unwanted solid materials from passing therethrough, the filtration vessel including a flexible liner for receiving the cell culture harvest solution and in fluid communication with the at least one candle filter.

In some embodiments, the apparatus comprises an actuator for collapsing the flexible liner. In some embodiments, the filtration vessel comprises a rigid or semi-rigid outer container for receiving the flexible liner. In some embodiments, the flexible liner includes a drain associated with a valve. In some embodiments, the flexible liner includes an agitator, or the at least one candle filter is suspended within the flexible liner. In some embodiments, the filtration vessel includes a vent in fluid communication with an interior compartment of the flexible liner.

This disclosure also pertains to an apparatus used to form a system in combination with a collection vessel for receiving the filtrate, and a backflush source including a backflush fluid and fluidly connected to the filtration vessel via the at least one filter, said backflush source, during backflush operation, adapted to supply backflush fluid back through the at least one filter for removing the cake formed on the filter. The backflush source may include a flexible liner, and the actuator may be adapted for collapsing the flexible liner of the backflush source.

According to still a further aspect of the disclosure, a system for clarifying a cell culture harvest solution, including target molecules and dynamic filter media is provided. The system comprises a filtration vessel including at least one filter, such as a candle filter, having a surface on which the dynamic filter media accumulates into a cake, said cake and at least one filter adapted, during normal operation, to permit a filtrate including target molecules to pass therethrough and said cake, during normal operation, adapted to prevent unwanted solid materials from passing therethrough; and a backflush vessel including a flexible liner for containing a backflush fluid and fluidly connected to the filtration vessel via the at least one filter, said backflush vessel, during backflush operation, adapted to supply backflush fluid back through the at least one filter for removing the cake formed on the filter, the backflush vessel including a flexible liner.

Yet another aspect of the disclosure relates to a system for clarifying a cell culture harvest solution, including target molecules and dynamic filter media. The system comprises a filtration vessel including at least one filter, such as a candle filter, having a surface on which the dynamic filter media accumulates into a cake, said cake and at least one filter adapted to permit a filtrate including target molecules to pass therethrough and said cake adapted to prevent unwanted solid materials from passing therethrough; and a backflush source fluidly connected to the filtration vessel via the at least one filter, said backflush source adapted to receive filtrate from the filtration vessel and supply the filtrate back through the at least one filter for removing the cake formed on the filter.

Still a further aspect of the disclosure relates to a system for clarifying a cell culture harvest solution, including target molecules and dynamic filter media. The system comprises a filtration vessel including a first disposable liner and at least one filter, such as a candle filter, having a surface on which the dynamic filter media accumulates into a cake, said cake and at least one filter adapted to permit a filtrate including target molecules to pass therethrough and said cake adapted to prevent unwanted solid materials from passing therethrough, and a backflush source fluidly connected to the filtration vessel via the at least one filter, the backflush source comprising a second disposable liner.

Yet a further aspect of the disclosure relates to a system for clarifying a cell culture harvest solution, including target molecules and dynamic filter media. The system comprises a compressible filtration vessel including at least one filter, such as a candle filter, having a surface on which the dynamic filter media accumulates into a cake, said cake and at least one filter adapted to permit a filtrate including target molecules to pass therethrough and said cake adapted to prevent unwanted solid materials from passing therethrough, and a backflush source fluidly connected to the compressible filtration vessel via the at least one filter. In some embodiments, the backflush source comprises a compressible backflush vessel.

A further aspect of the disclosure relates to a system for clarifying a cell culture harvest solution, including target molecules and dynamic filter media. The system comprises a filtration vessel including at least one filter, such as a candle filter, having a surface on which the dynamic filter media accumulates into a cake, said cake and at least one filter adapted to permit a filtrate including target molecules to pass therethrough and said cake adapted to prevent unwanted solid materials from passing therethrough; and a compressible backflush vessel fluidly connected to the compressible filtration vessel via the at least one filter. In some embodiments, the filtration vessel comprises a compressible filtration vessel.

In any disclosed embodiment, the system may form part of a microfacility.

BRIEF DESCRIPTION OF THE DRAWING FIGURES

Figure 2A:
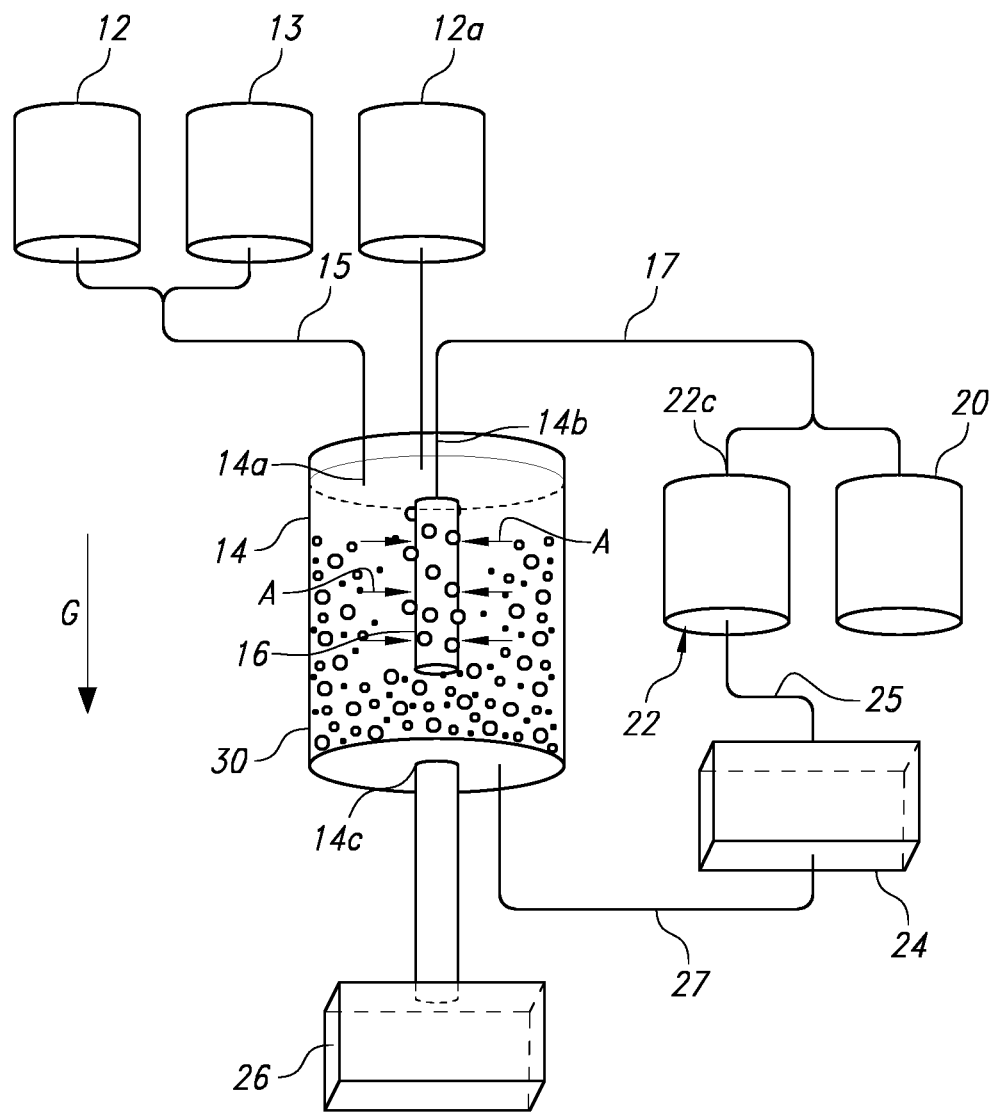
Figure 2B:
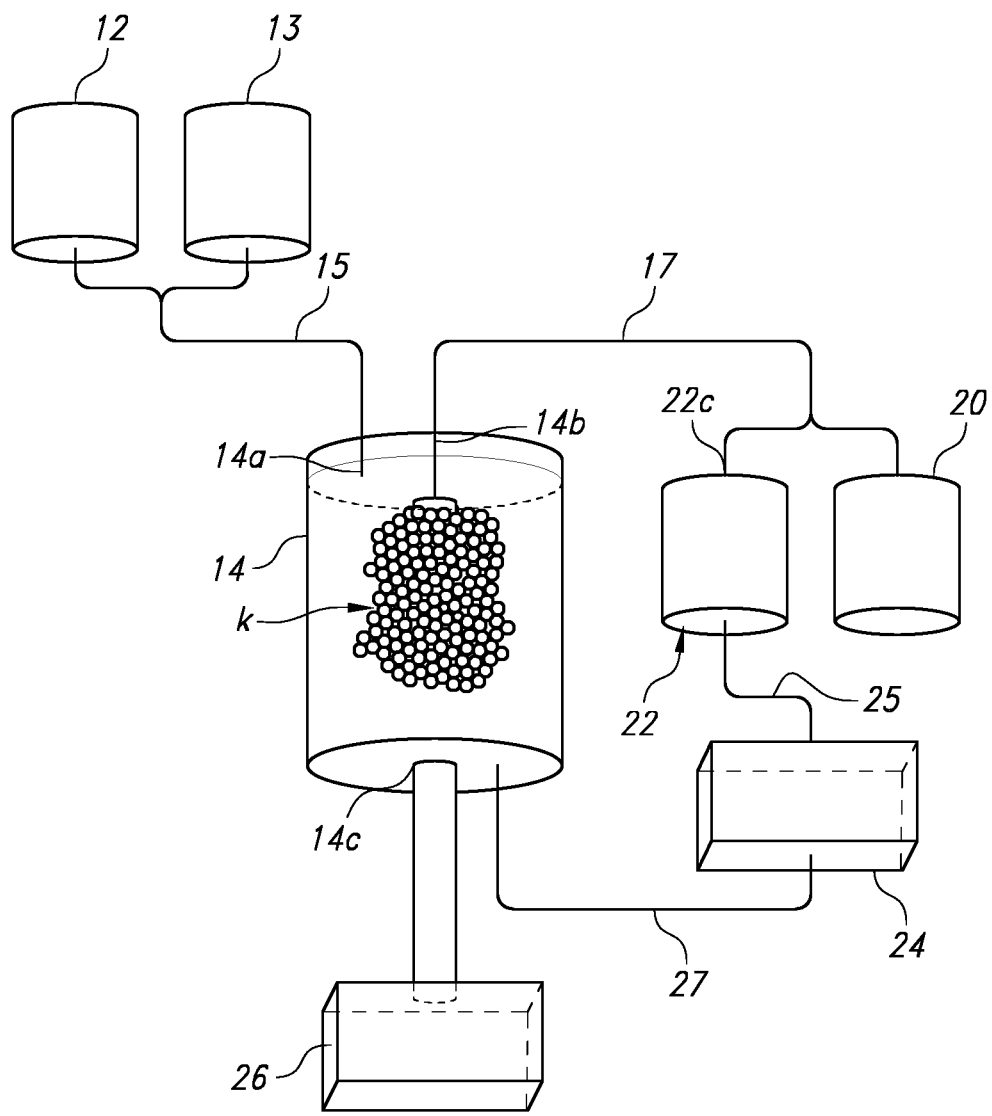
Figure 2C:
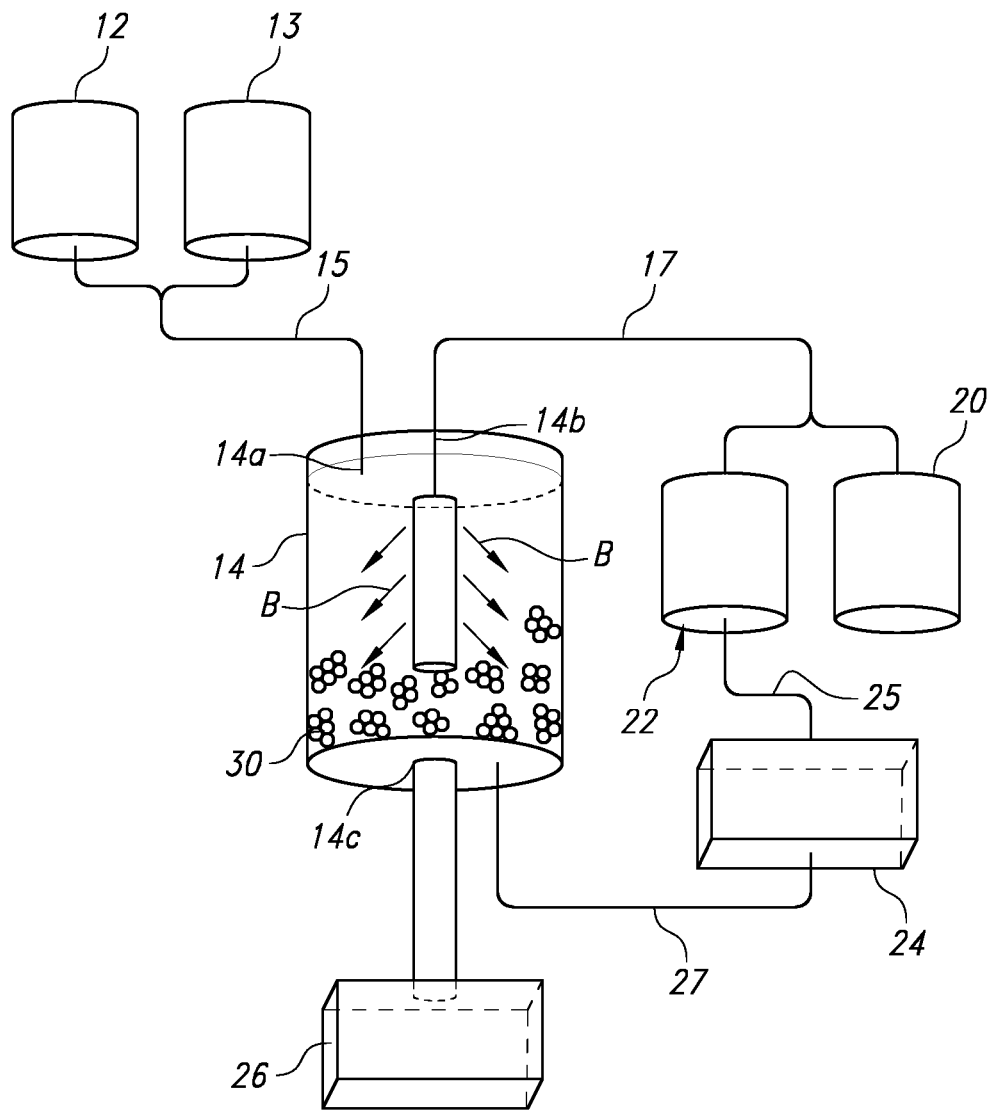
Figure 12:
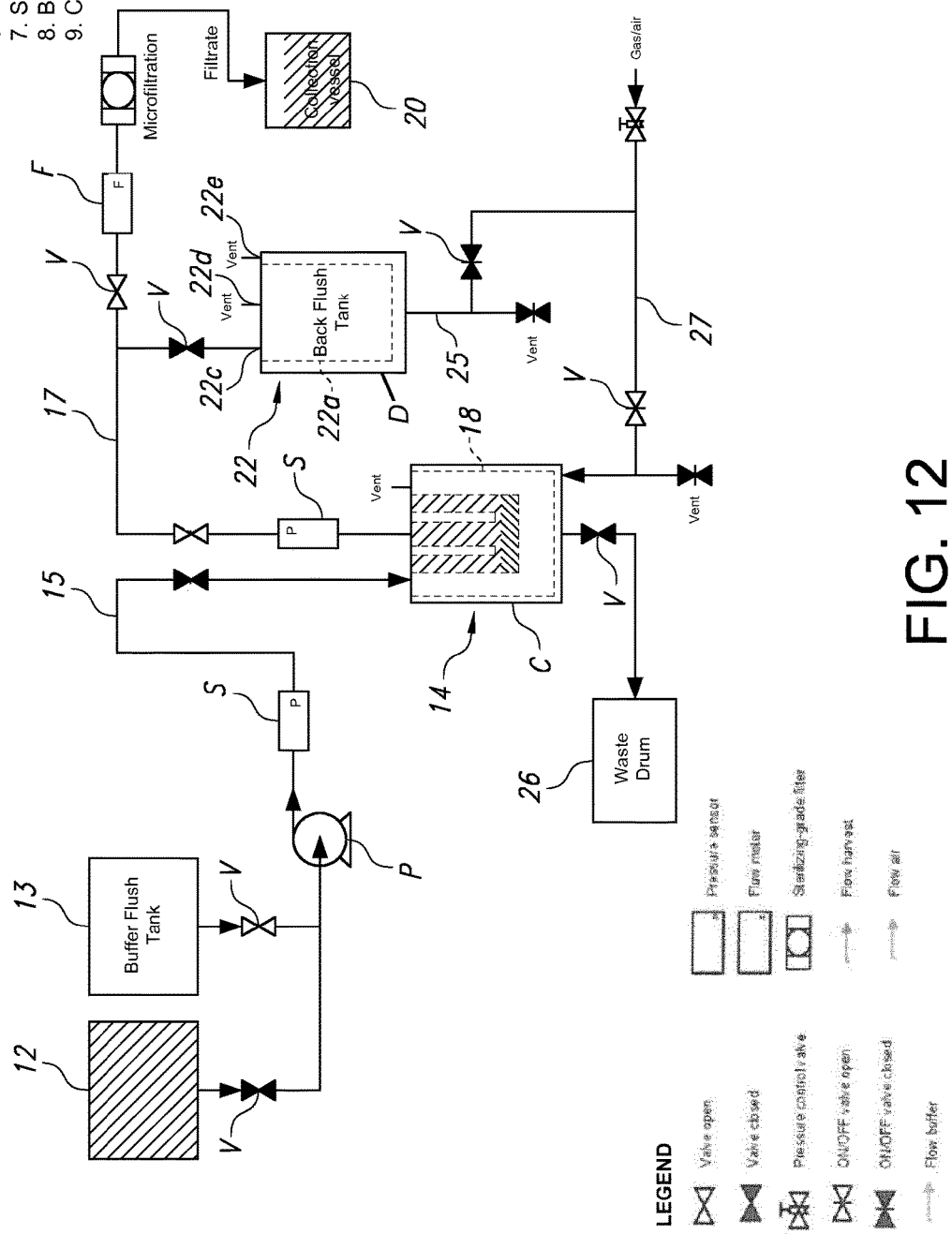
Figure 13:
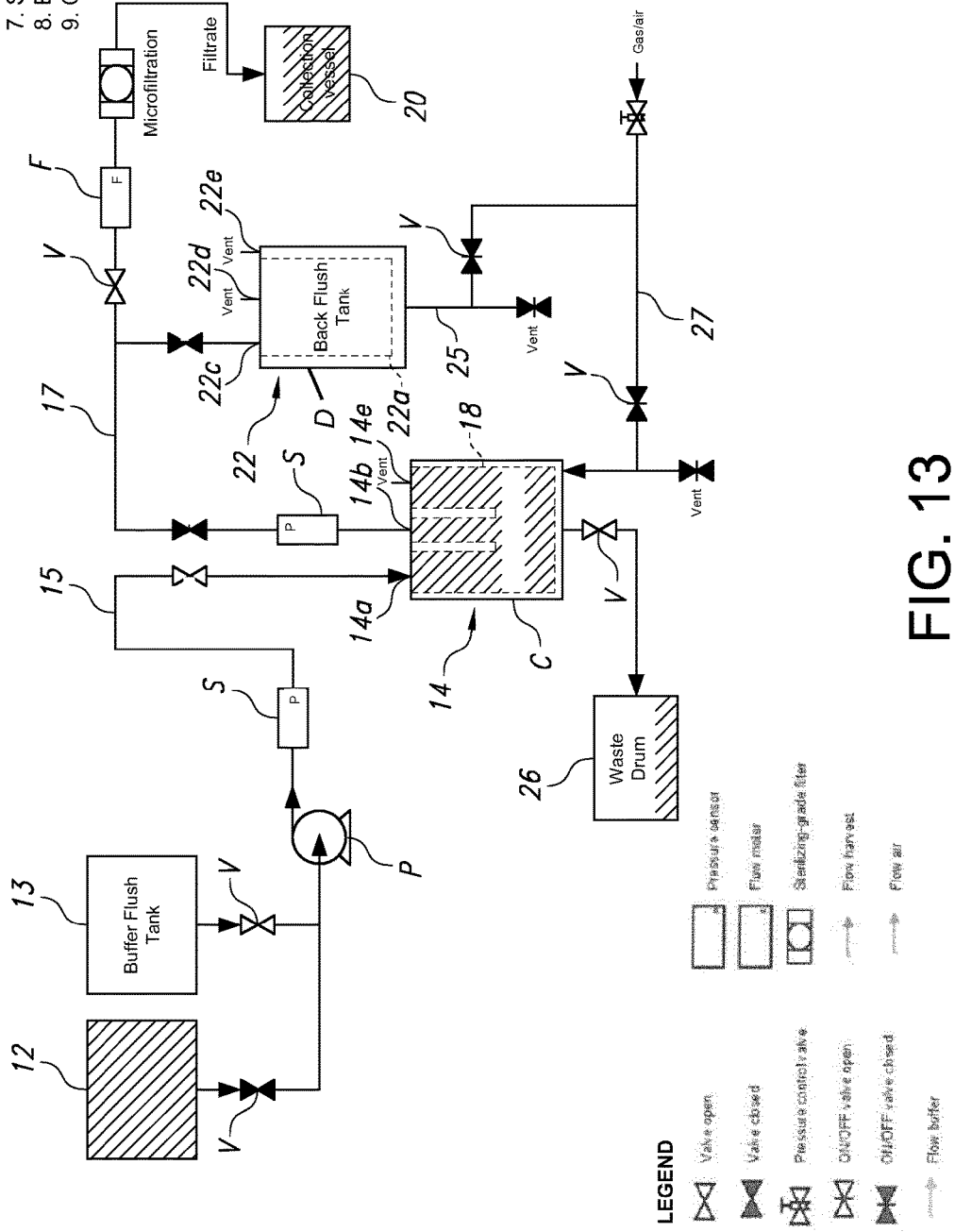
Figure 14:
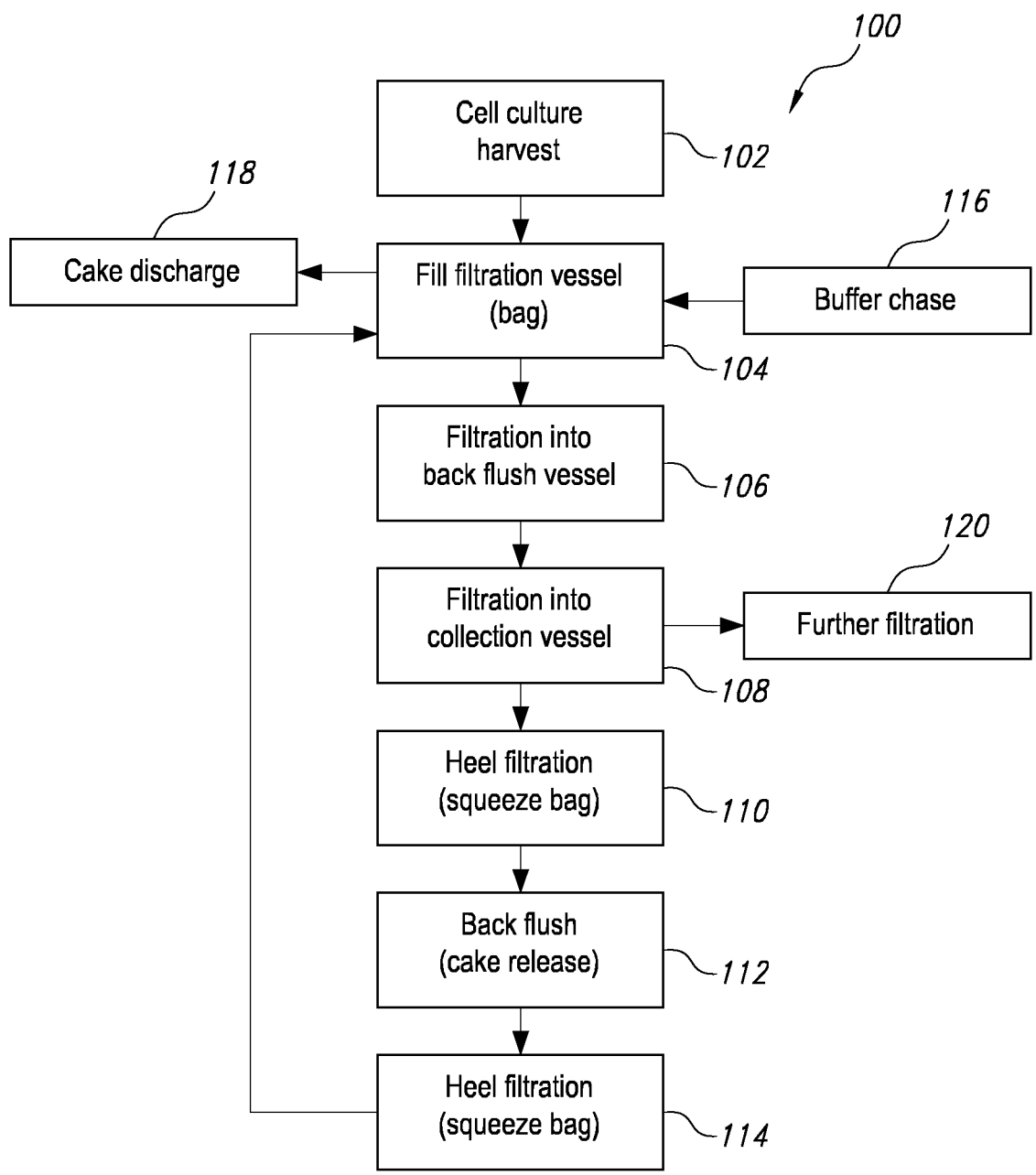

FIGS. 2A, 2B, and 2C are schematic views of one embodiment of the system according to the disclosure;

FIGS. 3-13 illustrate a clarification cycle according to an embodiment of the disclosure; and FIG. 14 is a flow chart, which includes the sequence of events depicted in FIGS. 3-13.

DETAILED DESCRIPTION

In one embodiment, a system disclosed herein comprises a filtration vessel comprising a flexible liner, disposed within a rigid or semi-rigid container and at least one filter disposed within the flexible liner having a surface adapted for separating a solid material from a liquid material, the filtration vessel being adapted for applying a pressure difference between the rigid or semi-rigid container and the flexible liner and/or the at least one filter and a downstream collection or backflush vessel, the filtration vessel being further adapted for removing solid waste from the flexible liner. In some embodiments the filtration vessel and the flexible liner comprise a port. The liner and vessel may be sealed together using a common component, such as for example a lid or cover. In some embodiments the port comprises a valve. In some embodiments the filtration vessel is adapted for pressure dispense operation. In some embodiments the system is housed in a microfacility.

In another embodiment, a method disclosed herein comprises adding a mixture comprising a liquid and a solid to the filtration vessel, applying a pressure difference between the interior of the rigid or semi-rigid container and the flexible liner to produce solids retained on the filter and a filtrate and backflushing the solids from the filter with a rinsing liquid or the filtrate and removing the solids from the flexible liner through a port in the liner. In some embodiments the port comprises a valve. In some embodiments the filter is regenerated. In some embodiments the filter is reused. In some embodiments the method further comprises an upstream process. In some embodiments the method further comprises a downstream process. In some embodiments, the method is performed in a microfacility.

In another embodiment, a system disclosed herein comprises a manifold adapted to connect with a source of fluid in need of filtration, a dynamic filter media, and a filtration vessel. The filtration vessel comprises a flexible liner, disposed within a rigid or semi-rigid container and at least one filter disposed within the flexible liner having a surface adapted for separating a solid material from a liquid material, the filtration vessel being adapted for applying a pressure difference between the between the rigid or semi-rigid container and the flexible liner and/or the at least one filter and a downstream collection or backflush vessel, the filtration vessel being further adapted for removing solid waste from the flexible liner. In some embodiments the filtration vessel and the flexible liner comprise a port. The liner and vessel may be sealed together using a common component, such as for example a lid or cover. In some embodiments the port comprises a valve. In some embodiments the filtration vessel is adapted for pressure dispense operation. In some embodiments the manifold is housed in a microfacility.

In another embodiment one or more steps in the aforementioned method are repeated. In some embodiments the system or one or more of its components are disposable. Preferably, the flexible liner is disposable.

Figure 1:
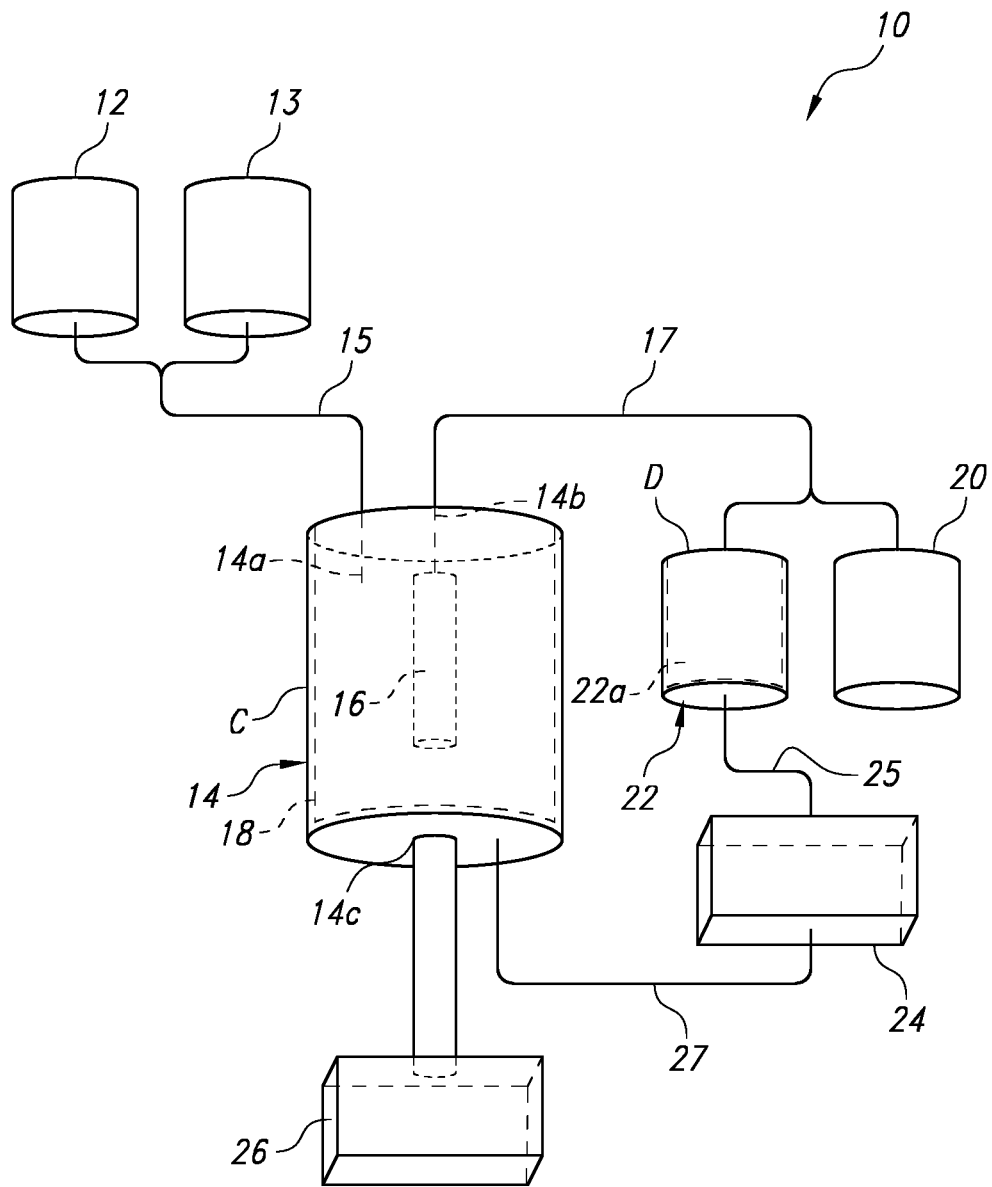
FIG. 1 is schematic view of one embodiment of the clarification system according to one embodiment.

FIG. 1 illustrates the concept of a clarifying system 10 of the present disclosure in an illustrative embodiment. In the embodiment, a cell culture harvest solution or "feed" source 12 is provided. As disclosed in PCT/EP2018/058366, feed source 12 may be a bioreactor (such as, for example, a high cell density fixed bed or suspension bioreactor) or it may be a different vessel downstream from a bioreactor. In any case, feed source 12 is arranged to hold (in the case of it being a vessel) and act as a source of a cell culture harvest solution comprised of a cell culture harvest that requires subsequent clarification, and may further comprise filtration, to recover a product of interest. Feed source 12 (of which there may be more than one, and feeding may be done in a continuous, semi-continuous or batch mode) is thus connected by feed conduit 15 to a filtration vessel 14 via an inlet 14a. The filtration vessel 14 is thus downstream of the feed source 12. The feed conduit 15 may also communicate with one or more sources 13 for providing source materials used in processing the cell culture harvest. Source 13 may comprise a buffer for a washing/chasing the solution. The buffer source 13 may simply be a source of water (such as water for injection). In one or more embodiments, the cell culture harvest may comprise one or more compounds allowing the formation of floccules, including but not limited to fatty acids having 7 to 10 carbon atoms and derivatives thereof, ureides and electropositive compounds.

The filtration vessel 14 may also include a filtrate outlet 14b at any location through which the clarified feed or "filtrate" from the filtration vessel 14 flows. This filtrate includes target molecules or cells of interest for subsequent downstream processing and/or collection (such as if the filtrate is the product of interest). The filtration vessel includes one or more protruding finger-like or "candle" filters, which may be in any suitable form to reach into the inner volume of the filtration vessel and form a filter surface area. One form of candle filter (as shown in FIG. 1) is a vertically oriented (extending in a direction from top toward bottom of vessel), filter. While a vertical orientation suspended from a top wall of the vessel 14 (or an associated structure) is shown, the candle filter 16 may project from any wall of the vessel 14 (including a sidewall or a bottom wall).

The surface area of the candle filter 16 for achieving filtration is provided along the exterior surface of the sides thereof. The candle filter 16 can be made of a polymer material (e.g., polyethylene) with a porosity that allows retention of filter aid (or dynamic filter media) particles, while allowing permeation of the liquid phase (i.e., the filtrate). In FIG. 1, the candle filter 16 is suspended from the top within the filtration vessel 14 and thus is fixed to and depends from an upper portion thereof. In alternative embodiments, the candle filter 16 could also be located along other portions of the vessel (e.g., the side or bottom wall). Locating the filter in a position farthest from the bottom of the vessel has advantages that will be described below. Accordingly, the filter 16 is considered static, in the sense that it is not free or unrestrained to travel about the vessel 14. Although shown in FIG. 1 to include a single candle filter 16, more than one filter may be provided, as outlined further in the description that follows.

The filtration vessel 14 may comprise a rigid or semi-rigid container C, but could be flexible as well (e.g., a bag-in-bag arrangement). It may be made of plastic or metal or any other suitable material known to one skilled in the art. In order to make a disposable arrangement that does not require cleaning or validation, the filtration vessel 14 may include an inner, flexible or collapsible liner, which may take the form of a bag 18 as indicated in the broken lines (e.g., a single-use, two or three-dimensional flexible polymeric bag in any suitable configuration comprising chemically resistant materials). The bag 18 may be disposed within the rigid or semi-rigid container C, and thus form the filtration vessel as an assembly (that is, an inner disposable vessel for receiving the cell culture harvest solution from the upstream feed source 12, and also an outer (possibly reuseable) vessel that may receive a fluid (air) for compressing or squeezing the bag 18 to reduce its volume and cause liquid therein to flow through the candle filter(s) 16 (which as discussed below may include an accumulated cake of a dynamic filter media).

Figure 1A:
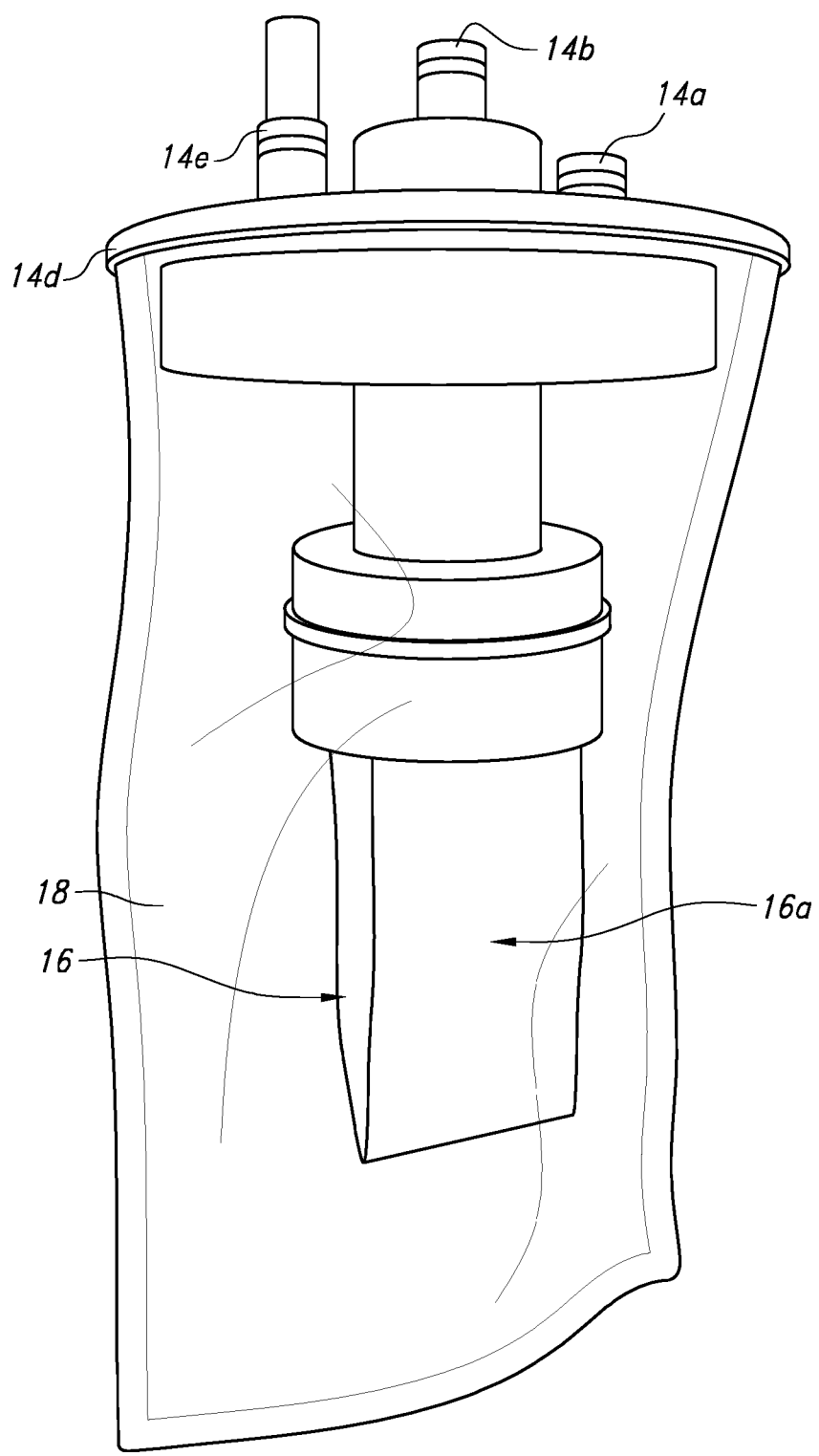
FIG. 1A illustrates one embodiment of a disposable filtration vessel.

FIG. 1A illustrates one particular example of a candle filter 16 positioned in a flexible bag 18 for forming the feed receiving portion of the filtration vessel 14. The rigid outer container within which the bag 18 is disposed is not shown. In this example, the candle filter 16 comprises two spaced candle filters, each of which comprises a filtration media 16a (e.g., polyethylene having a selected porosity, such as for example 0.7 microns). The filtration media 16a may be elongated and/or slender, forming a finger-like structure along the exterior surface of the candle filter 16, and could also be located within the candle filter 16. The end of the candle filter (distal from the top of the vessel 16) may be tapered and may be formed by simply bonding the ends of the material together. This allows for the candle filter 16 to be positioned in the vessel 14 so as to project from the top (or side) thereof into the vessel volume. Thus, the media 16a is designed and located to be subject to having a cake filter formed on the surface thereof. The filtration media 16a may extend over a support (not shown), which may comprise a mesh, grid, or like porous material to provide rigidity and prevent the filter media from collapsing. The media may attach to the support using an adhesive or other suitable means for attachment or binding. The bag 18 may be welded or otherwise attached to lid 14d (such as along a depending extension of it) for sealing and enclosing the candle filter 16 against unwanted ingress. The candle filter 16 (at the end proximal to the vessel top) is fluidly connected to outlet 14b. The lid or top portion 14d may also include the inlet 14a, the outlet 14b, and vent 14e (which may be aseptic/sterile or non-aseptic) for the filtration vessel 14, as shown, and also serves as a closure for the filtration vessel 14 (and bag 18 in particular, which may be peripherally bonded to the body of the lid 14d to create a fluid-tight seal).

The bag 18 may also include an outlet or drain for discharging waste, which may be associated with a valve for allowing for the selective discharge (see, e.g., FIGS. 3-13). The filtration vessel 14 can be sized quite small (e.g., in one example 1.5 to 1.8 L) but could also be used with a larger feed source (e.g. up to 200-500 L bioreactor). The size of the filtration vessel is scalable to the size of the upstream process. In some embodiments the system comprises a bioreactor having a volume from 1.5 L to 1000 L, preferably from 10 L to 750 L and more preferably from 200 L to 500 L.

The outlet 14b may communicate, through filtrate conduit 17, with a filtrate collector, such as a collection vessel 20. This collection vessel 20, in operation, receives the filtrate travelling from the filtration vessel 14 via the one or more filters 16. A backflush source may also be provided (along with suitable valving) via the filtrate conduit 17. The backflush source may be a backflush vessel 22 containing backflush liquid (e.g., water (including ultrapure water, USP water, EFI) or equilibration buffer (e.g., PBS or HBS)).

The backflush vessel 22 is used (via conduit 17) to introduce the backflush fluid (meaning liquid or gas (e.g., compressed air) back through the candle filter 16 in reverse direction (that is, from the outlet 14b for delivering the filtrate to the collection vessel 20, which could alternatively be used as a backflush source instead of vessel 22). This permits the reusability or regeneration of the candle filter(s) 16 (before the media buildup begins to negatively affect flow rate through the filter 16) so that more feed can be supplied to the filtration vessel 14 and fed through filter 16. As discussed below, the backflush fluid may be sourced from the filtrate of the feed source 12 or from the buffer source 13 or some other source. One embodiment includes some portion of the filtrate to be transmitted to the backflush vessel to be used for the backflush fluid. Importantly, this effectively simplifies the process (as opposed to using a buffer or other liquid for backflushing) as no adjustments need to be made to the process or solution due to the common backflush fluid introduction.

Figure 1B:
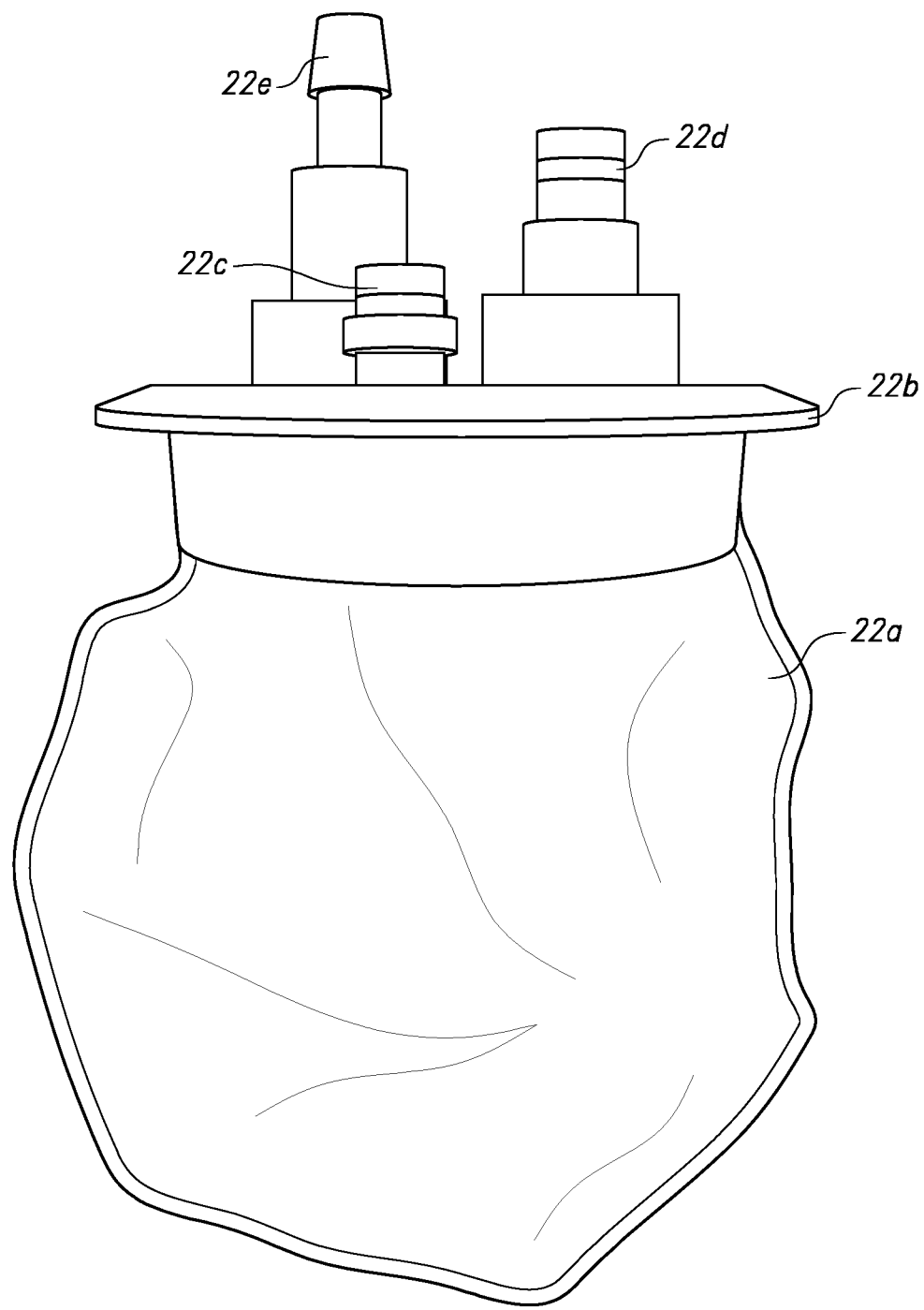
FIG. 1B illustrates one embodiment of a disposable backflush vessel.

As indicated in FIG. 1B, the backflush vessel 22 may comprise an inner, flexible or collapsible liner, which may take the form of a bag 22a. The bag 22a may be connected to a rigid lid or top portion 22b that may also include a port 22c serving as a fluid inlet or outlet, a first outlet or vent 22d in communication with the interior compartment of the bag 22a, and a second outlet or vent 22e for communicating with a space external to the bag 22a. The lid 22b thus serves as a closure for the backflush vessel 22 (and bag 22a in particular, which may be peripherally bonded to the body of the lid 22b to create a fluid-tight seal). The bag 22a may be provided in a rigid or semi-rigid container D (see FIG. 1), thus forming the backflush vessel 22 as an assembly (that is, an inner disposable vessel for receiving a backflush fluid, which as noted above may be a portion of the filtrate, and also an outer vessel, which as noted below may receive a fluid (air) for compressing or squeezing the inner vessel to reduce its volume and cause liquid therein to flow through the candle filter(s) 16) in reverse). The size of the backflush vessel 22 can be quite small (e.g. in one particular example 1.0 to 1.2 L) to hold only enough fluid (in this case, filtrate) to accomplish the backflush function during backflush operation, but is easily scalable to meet the requirements of a particular arrangement in which it is used. The impetus for forcing the backflush liquid to flow into the filtration vessel 14 may be an actuator. In the illustrated embodiment the actuator takes the form of a gas source 24, such as a vessel containing gas under pressure (e.g., compressed air), which is delivered to the backflush source 22 via conduit 25, but could also be mechanical in nature (e.g., a piston or pump). As shown in FIG. 1, this gas source 24 may also be connected via a conduit 27 to the filtration vessel 14 to introduce a fluid (gas) between the bag 18 and the inner wall of the filtration vessel 14 to cause the former to collapse and thus force liquid to flow through the candle filter 16 to the outlet 14b to the collection vessel 20 (which, as noted below, may be repeated during the overall clarification process).

The filtration vessel 14 may also include a waste outlet or drain 14c, which may be connected to or associated with a waste collector or vessel 26. However, the waste could also be ejected or recovered from the filtration vessel 14 in other ways (such as, for example, by applying suction to a dip tube or the like projecting into the filtration vessel). The filtration vessel 14 may optionally include an agitator for use in agitating the contents, perhaps to maintain homogeneity of the solution, which agitator may operate in a non-contact manner (e.g., a magnetic impeller) or via a dynamic seal capable of maintaining sterile conditions). When flexible liner 18 is present agitation can be provided using a pressure differential.

In use, and with reference to FIGS. 2A-2C, the feed solution (which may contain the cell culture harvest and other materials including a filter aid or suitable dynamic filter media 30) may be delivered from the feed source 12 to the filtration vessel 14. The dynamic filter media 30 may include diatomaceous earth (DE), which is shown in suspension in FIG. 2A, and may be delivered from a separate source 11, as indicated in FIG. 1). The dynamic filter media 30 is introduced for the purpose of filtering certain undesirable impurities from the harvest solution such as cells, cell debris, or other waste products from the feed solution and passing downstream a clarified filtrate of the cell culture harvest solution, including the target molecule for further processing. Alternatively, the dynamic filter media 30 may be added to the filtration vessel 14 separate from the feed solution, such as by providing it in the form of a slurry from an auxiliary vessel 12a via a separate conduit 29 (as shown in FIG. 2A) or via shared conduit 15.

When extraction of the filtrate is desired, a pressure differential may be created, such as by using a pump (see, e.g., FIG. 3), As indicated in FIGS. 2A and 2B, this will generate a flow generally perpendicular to a lateral side surface of the candle filter 16 and also generally perpendicular to the direction of gravity G. In other embodiments where filters 16 are positioned within the vessel but arranged differently with respect to the vessel bottom, the flow can be generated in a direction otherwise not aligned with the direction of gravity, as would be the case with a bottom positioned filter with a purely horizontal surface). This flow will cause at least a portion of the dynamic filter media 30 to accumulate on the outer surfaces (lateral sides, but also possibly bottom if present) of candle filter 16 (see action arrows A for indicating the approximate direction of the flow transverse or opposite to the direction of gravity due to pressure differential). As a result, a cake K is formed that includes tortuous paths or tunnels which may act to block or filter the impurities or waste within the filtration vessel 14 as the filtrate is collected outside, but does not substantially block the pores of the underlying filtration media 16a of the candle filter 16.

Extraction of filtrate to the collection vessel 20 (or alternatively the backflush source 22, if provided with filtrate) may continue until the accumulated dynamic filter media 30 creates a layer on the candle filter 16 that eventually impedes flow to an undesirable level. This limit may be determined using a sensor, such as a flowmeter (see FIGS. 3-13), in the associated conduit 17. Using suitable valving and the source of pressurized gas 24, the backflush liquid may be caused to flow through the outlet 14b and via candle filter 16 into filtration vessel 14. As shown in FIG. 2C, this backflush action causes the dynamic filter media 30 to be dispersed back into suspension within the solution of the filtration vessel 14 (note action arrows B) with some of it eventually settling at the bottom of the vessel 14. Additional feed solution may be added from feed source 12, and the process can be repeated as often as desired or necessary to optimally clarify the harvest solution and collect the filtrate. An optional added step may be to introduce buffer from source 13 into the filtration vessel 14 to wash the dynamic filter media 30 that settles to the bottom of the vessel 14, which may be done to capture any target molecules hidden or trapped therein when the buffer is withdrawn through candle filter 16 using the same sequence. A buffer can be used to later wash the spent dynamic filter media 30 from the filtration vessel 14, as outlined further in the following description.

In situations where the above process is completed (or, at any time at which the level of dynamic filter media in the vessel is such that the efficiency of the candle filter(s) 16 might be hampered, such as if the level of dynamic filter media reaches the lower extent of the filter in the illustrated embodiment), any remaining waste product or dynamic filter media 30 may be discharged. This may involve introducing liquid (buffer) from the source 13 to promote flowability, which forms a slurry similar to wet sand (which, as discussed below, may optionally be further compacted or squeezed to cause liquid to flow through conduit 17 to collection vessel 20, and thereby enhance recovery of the target molecules of interest). The slurry may be discharged from the filtration vessel 14, such as via the waste outlet or drain 14c, and the clarifying process may be repeated by introducing a new batch of feed/cell culture harvest solution from the feed source 12.

As can be appreciated, this arrangement allows the dynamic filter media 30 and/or candle filter(s) 16 to be repeatedly regenerated for further use, as desired, in a simple and efficient manner until the waste on the bottom of the vessel grows in height to a point where it impedes the functioning of the candle filter(s) 16. In light of the ability to continuously reuse the candle filter 16 with the regenerated media 30, the ratio of filter area to the volume of production can increase considerably, as compared to a horizontal filter fixed at the bottom of a vessel. Also, the dynamic filter media 30 may be discharged from the filtration vessel 14 when desired via outlet or drain 14c. This permits the filtration vessel 14 to be designed and manufactured to a considerably smaller form factor (since being overwhelmed by the settled dynamic filter media 30 during a campaign is delayed). This smaller vessel will be much less expensive to produce and will facilitate a reduction of manufacturing footprint. Thus, the system 10 is readily adapted for use as an integral component of a limited space or "microfacility" for performing bioprocessing.

In the case where the filtration vessel 14 includes the inner liner or bag 18 in a rigid or semi-rigid outer container, a step may also be performed of causing the bag to collapse within the filtration vessel 14. This may be achieved using gas from the gas source 24 to enter the area in the space between the bag 18 and the rigid or semi-rigid container C of the filtration vessel 14 via conduit 27. This compression reduces the volume of the inner compartment of the bag 18, and thus forces feed solution or buffer within the bag 18 to exit via the outlet 14b, and also may compress or squeeze any dynamic filter media 30 present and not caked on the candle filter(s) 16. This step may be implemented when at least some of the dynamic filter media 30 is accumulated on the candle filter 16, as shown in FIG. 2B, such as during the initial filtering step, or after the backflush step is completed, as outlined in the following description.

Figure 3:
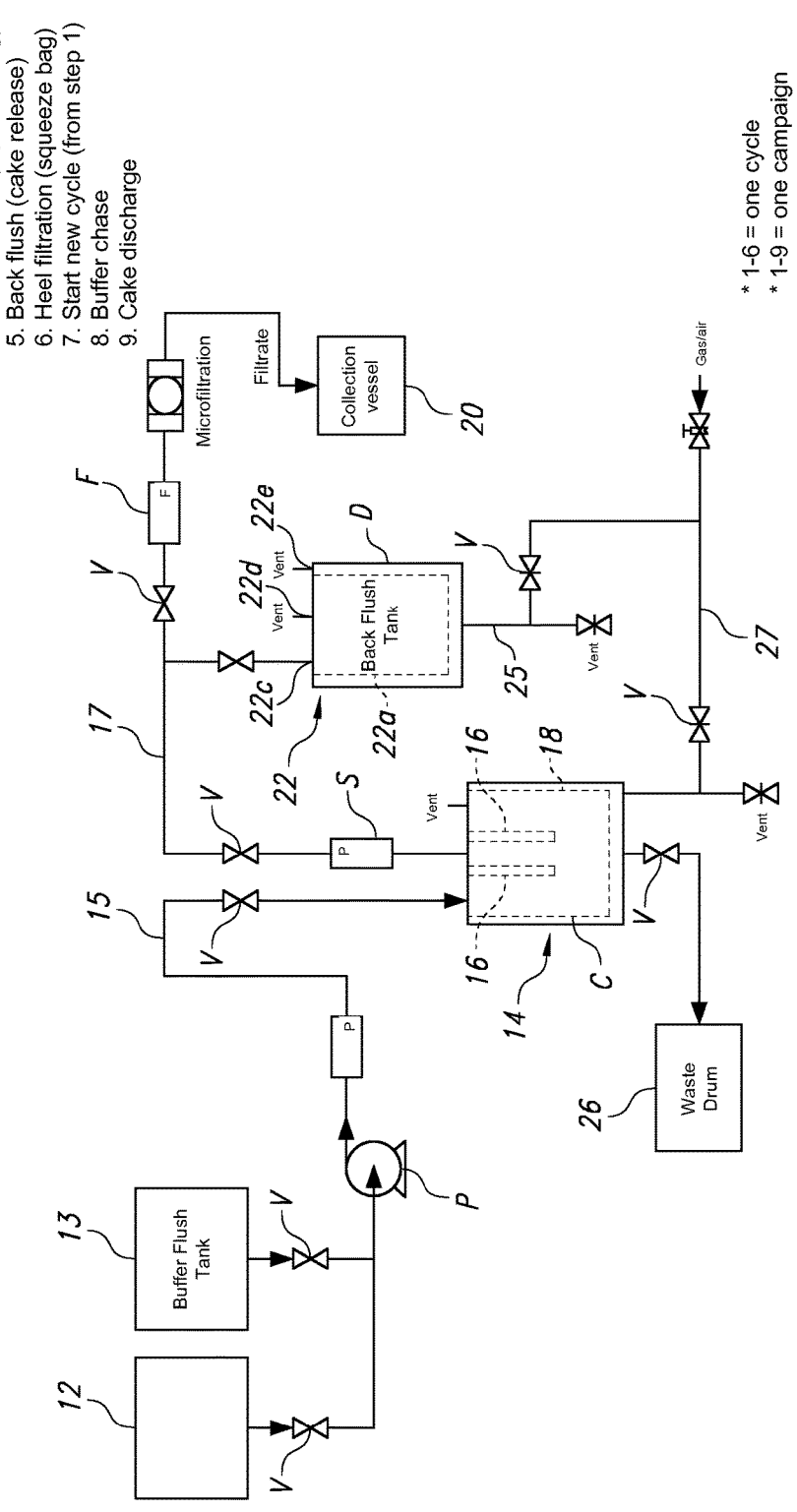

FIGS. 3-13 schematically illustrate the above-described system 10 and process in further detail, and FIG. 14 is a corresponding flow chart. Noteworthy from FIG. 3 is the presence of two candle filters 16 in the filtration vessel 14. As noted above, only one filter can be used and even more than two filters can be utilized when more filtration capability is required or sought.

Figure 4:
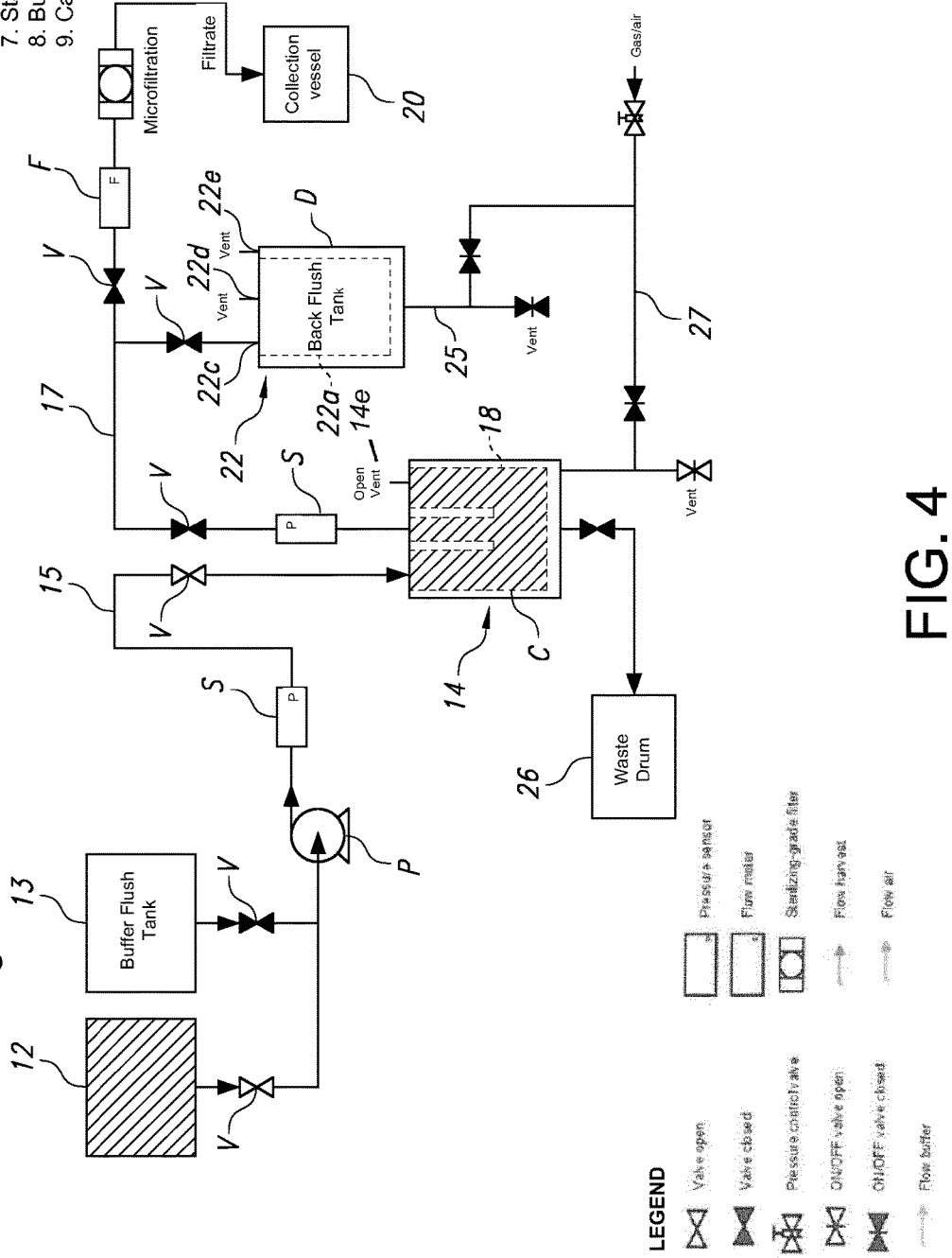

FIG. 4 illustrates a first step of filling the filtration vessel 14, which in the illustrated embodiment includes the flexible liner or bag 18. This may be achieved using a pump P to deliver the solution including a cell culture harvest and dynamic filter media from the upstream feed source 12 (10 L suspension bioreactor) by opening and closing corresponding valves V to establish fluid communication. A vent 14e associated with the filtration vessel 14 may be opened to allow for the liquid inflow. Pressure sensors S and flow meters F may be provided throughout the system 10 to regulate and monitor the flow of liquid throughout.

Once the filtration vessel 18 is provided with fluid (as shown in FIG. 4), the next step in the illustrated embodiment may be to fill the backflush vessel 22, if not already filled with liquid. The backflush vessel 22 may be partially or completely filled. This backflush vessel 22 may also include the liner or flexible bag 22a, as shown in FIG. 1B and may be quite small compared to the filtration vessel 14. Vent 14e may be closed during this step.

Figure 5:
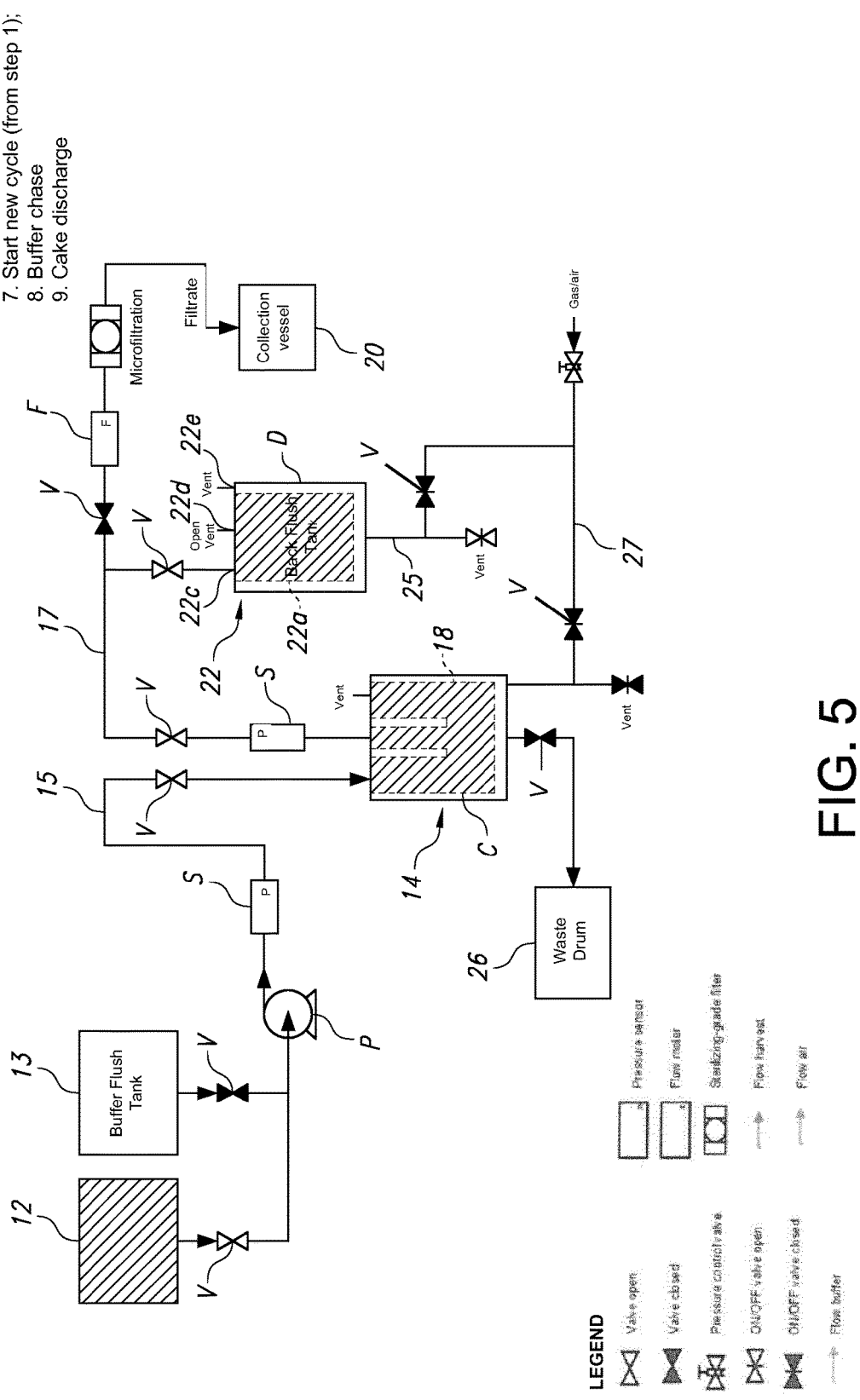
Figure 6:
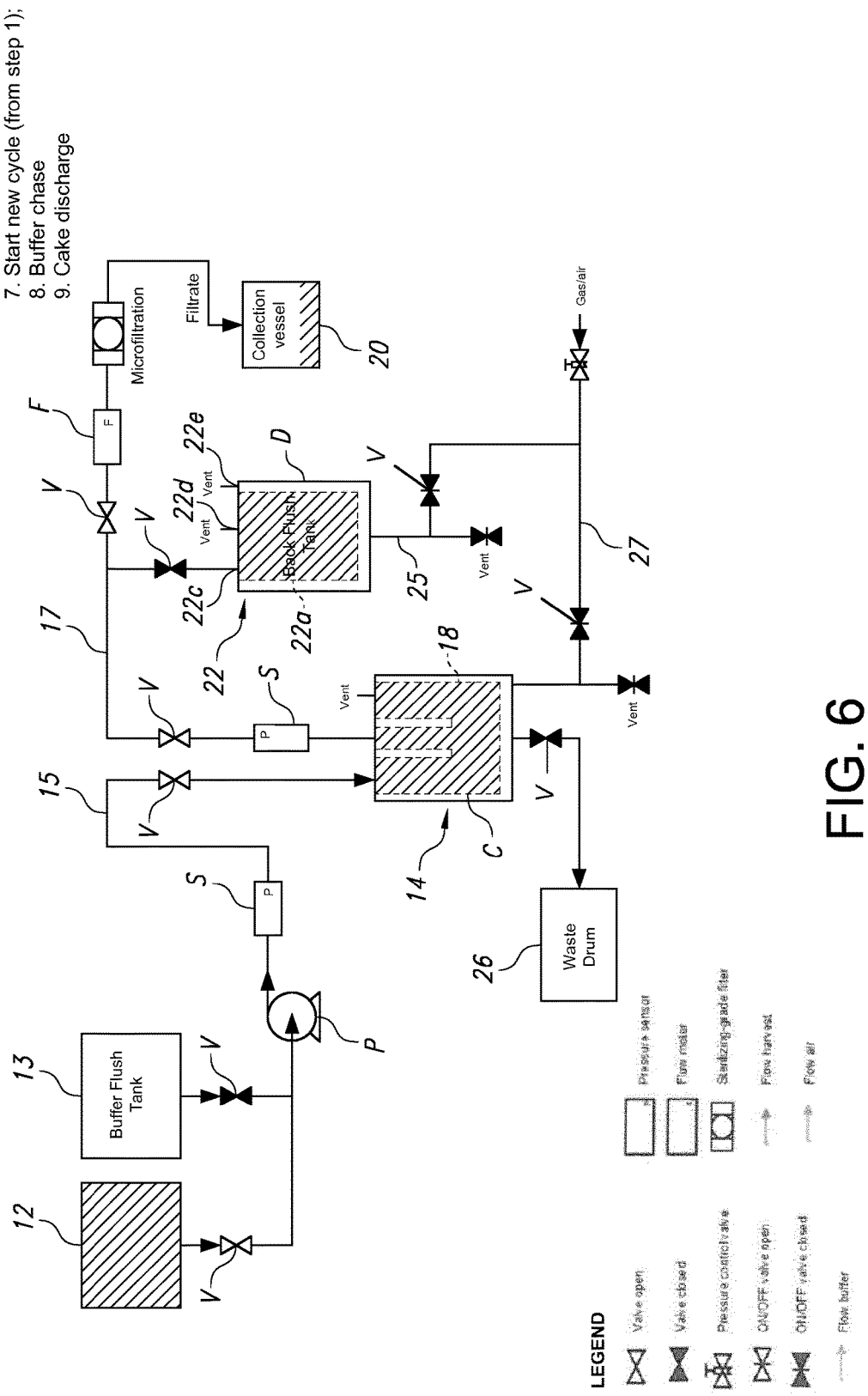

In one possible embodiment, this filling of the backflush vessel 22 may involve withdrawing liquid from the filtration vessel 14 itself, as indicated in FIG. 5 (by using a pump, or using pressure, or any combination thereof), and may involve opening the vent 22d associated with the backflush vessel 22 (and bag 22a in particular). Thus, the backflush vessel 22 contains filtrate in this situation, which may include the target molecules, but not the dynamic filter media 30. This embodiment provides the advantages of maintaining the same chemical environment rather than introducing a liquid that could affect the environment and require further adjustment. However, as noted below, buffer (e.g., from a prior cycle) may be provided to backflush vessel 22 instead of or in addition to the filtrate. After the backflush vessel 22 is sufficiently full from filtrate passing through the candle filters 16, additional filtrate making its way through the candle filters 16 may then be withdrawn from the filtration vessel 14 and redirected through conduit 17 to the collection vessel 20, as indicated in FIG. 6. In the course of this process, the cake (not shown) is thus formed on a surface of the filters 16.

Figure 7:
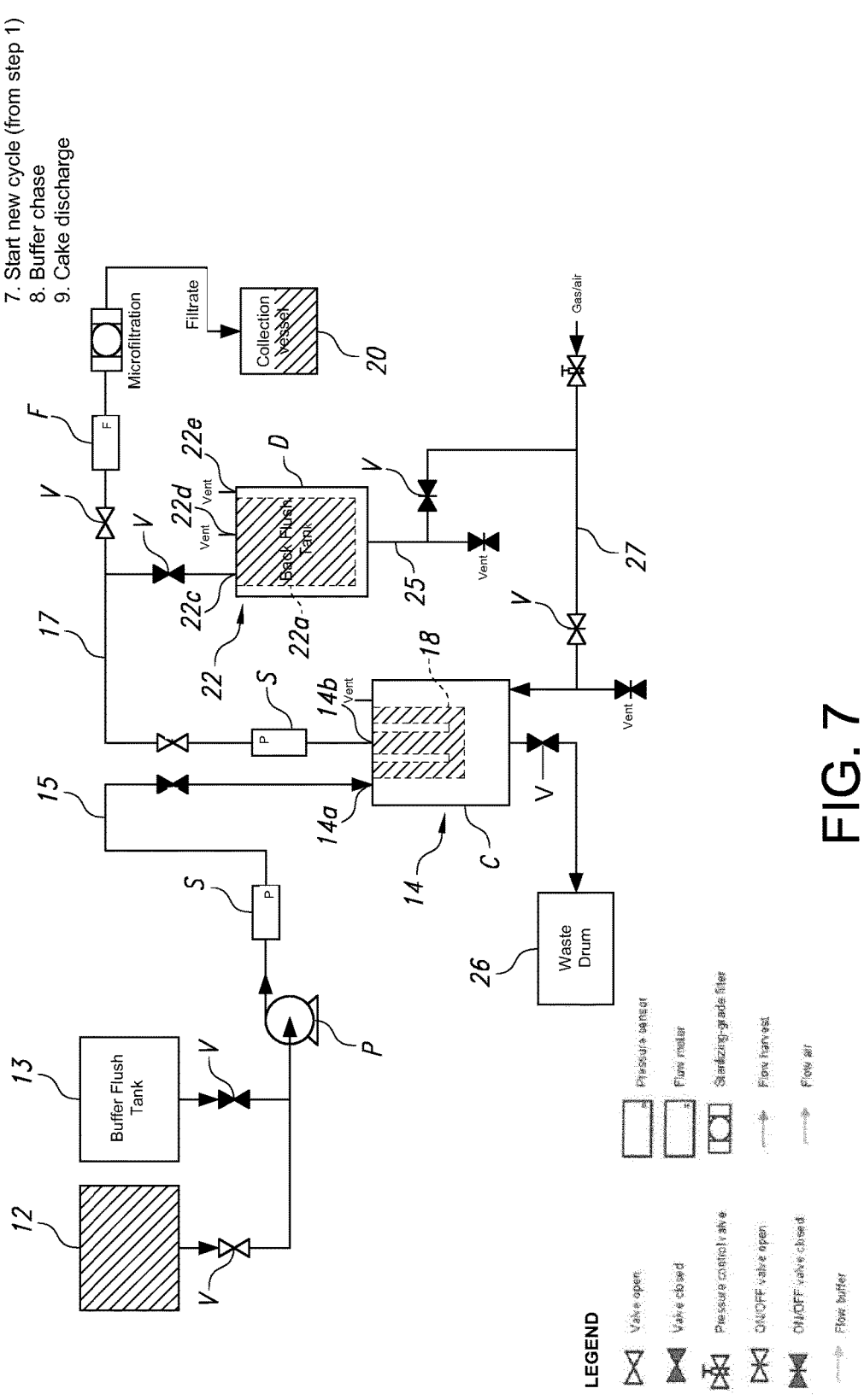
Figure 8:
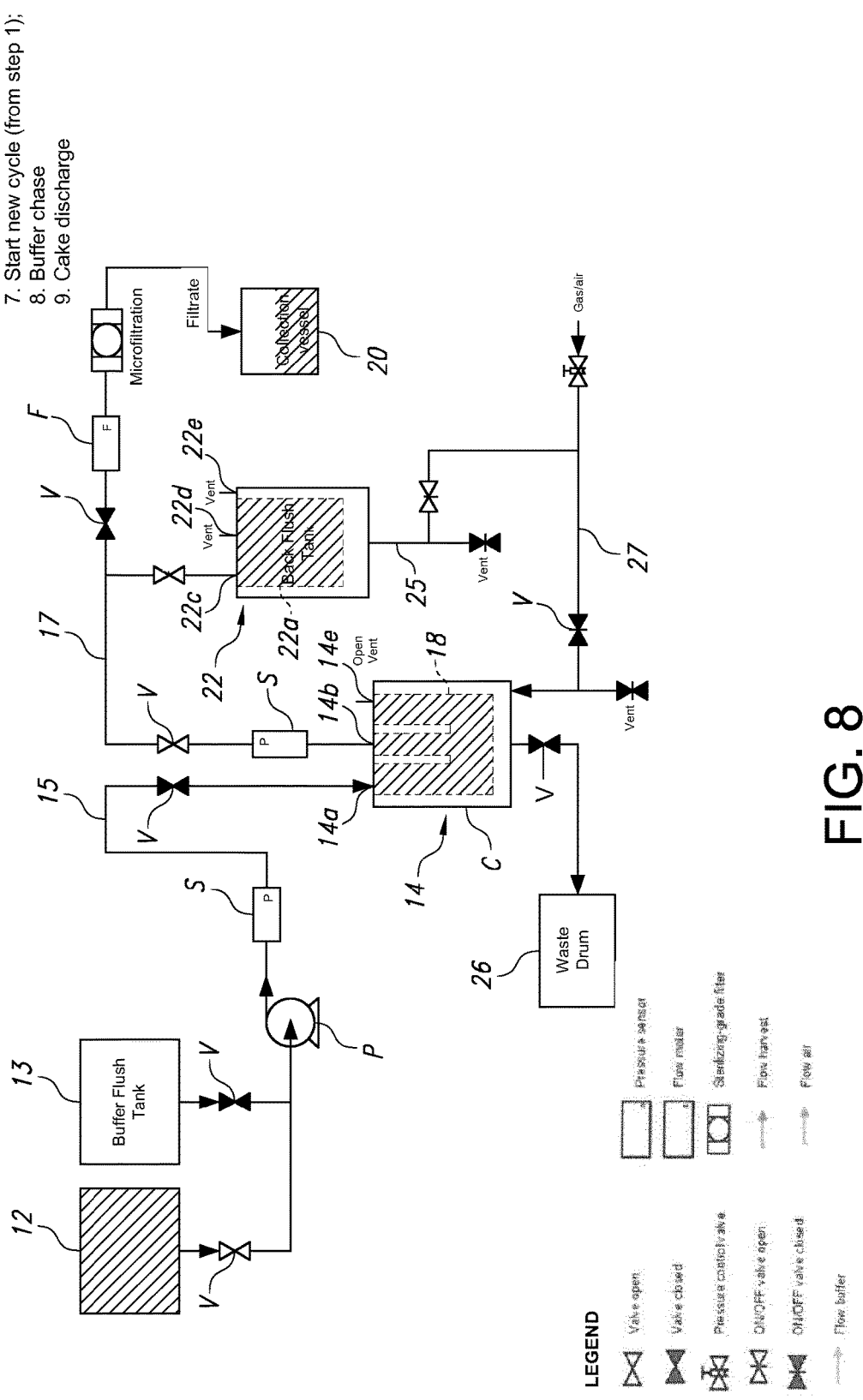

The bag 18 associated with the filtration vessel 14, which includes the dynamic filter media 30, may then be at least partially collapsed (FIG. 7). This may be done using compressed air provided to conduit 27 via source (not shown). This squeezing of the bag 18 is done to force remaining filtrate to the collection vessel 20.

When the evacuation of bag 18 is completed (which may be determined using flow meter F or visually), the backflush liquid may be delivered from vessel 22 (FIG. 8) to the filtration vessel 14, with vent 14e again opened to facilitate the inflow. The vessel 22 may be pressurized externally (e.g., squeezed by the application of external pressure in the case of a bag 22a), possibly using the same source of gas for causing the bag 18 to collapse (that is, provided via conduit 25 to the space between the vessel 22 and the liner or bag 22a, which may be in communication with vent 22e), but alternatively a different source can be used, as could a pump instead to withdraw the liquid. This compression of the liner or bag 22a delivers the backflush liquid in reverse through the filters 16 into the filtration vessel 14. This liquid flow serves to dislodge accumulated dynamic filter media 30 and waste from the filter surface, which is placed in solution again or permitted to settle at the bottom of the filtration vessel 14. This process regenerates the candle filter and provides for reuse of the dynamic filter media. New feed with or without additional dynamic filter media may also be added to the bag 18.

Figure 9:
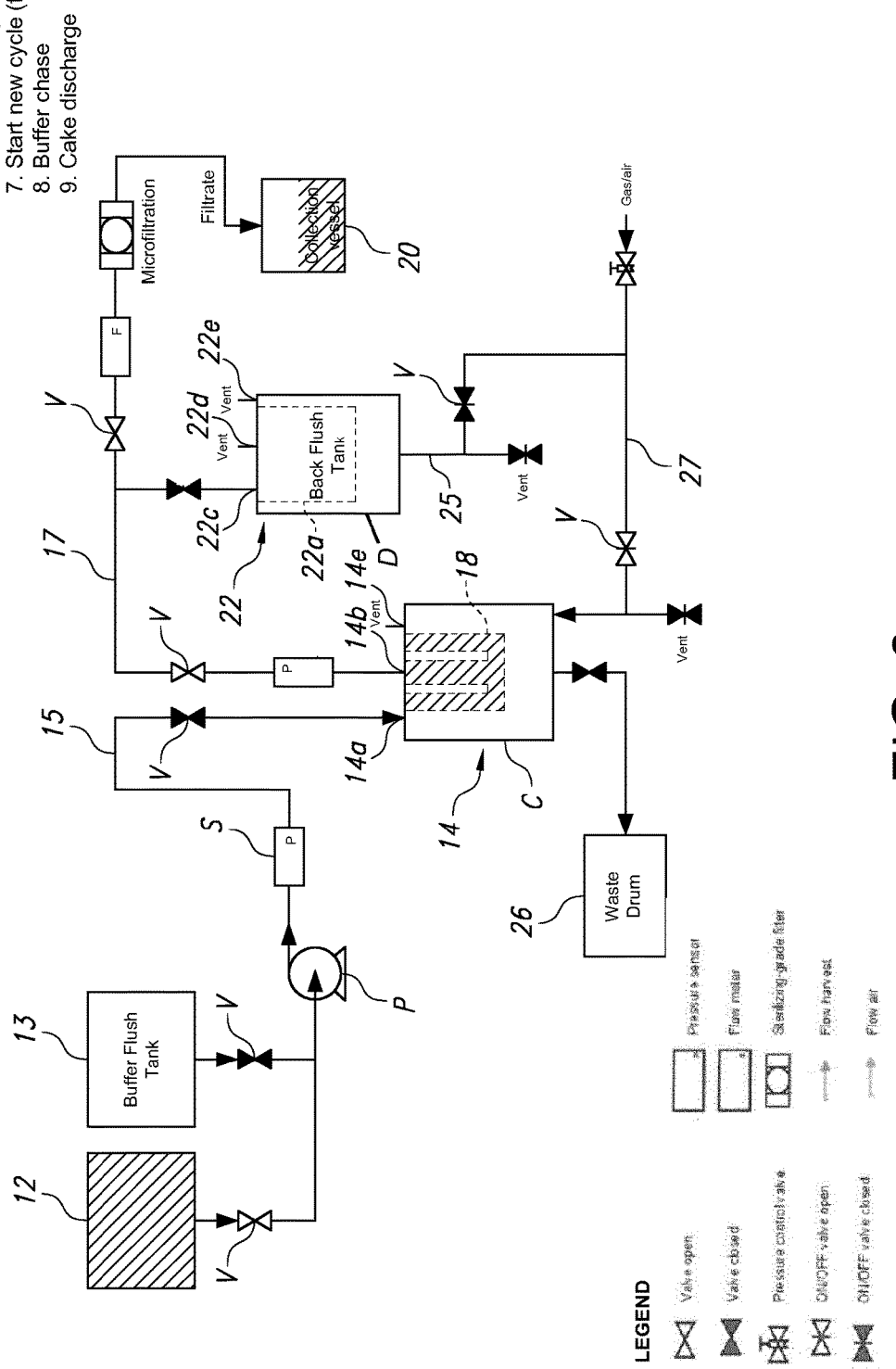
Figure 10:
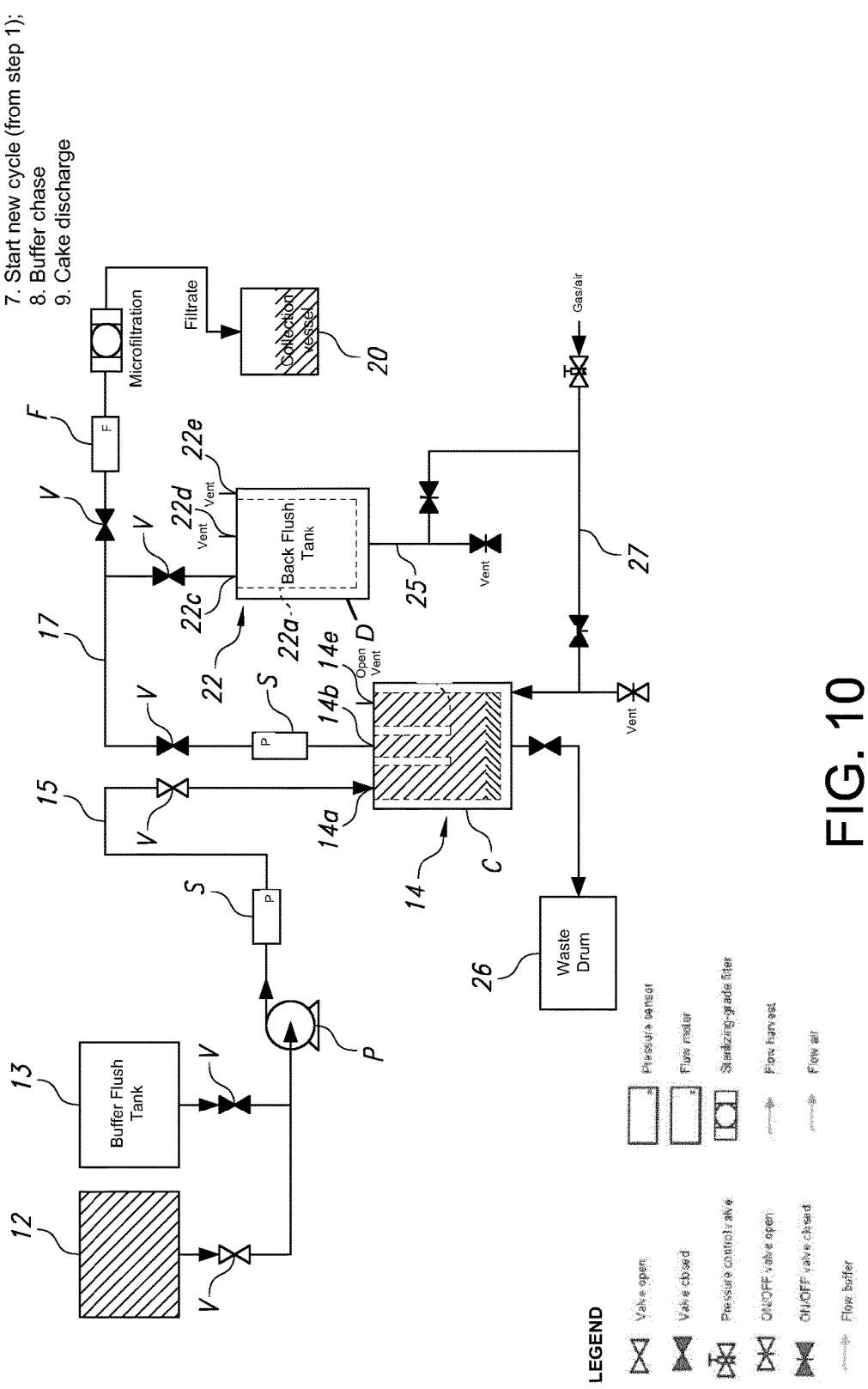

The bag 18 forming part of the filtration vessel 14 may then be caused to collapse again, as indicated in FIG. 9, which may be achieved by supplying fluid (air) via conduit 27 to the interior of vessel 14, with vent 14e closed. This squeezes and compacts the bag 18, and also any dynamic filter media 30 released from the filter surface (during the present cycle or a prior cycle), which at this stage is settled at the bottom with and has the consistency of wet sand. The resulting compaction and reduction in volume of the bag 18 forces the remaining "heel" of the vessel fluid through the filters 16 to be delivered to the collection vessel 20, and thus enhances the recovery of the target molecule or product of interest.

Figure 11:
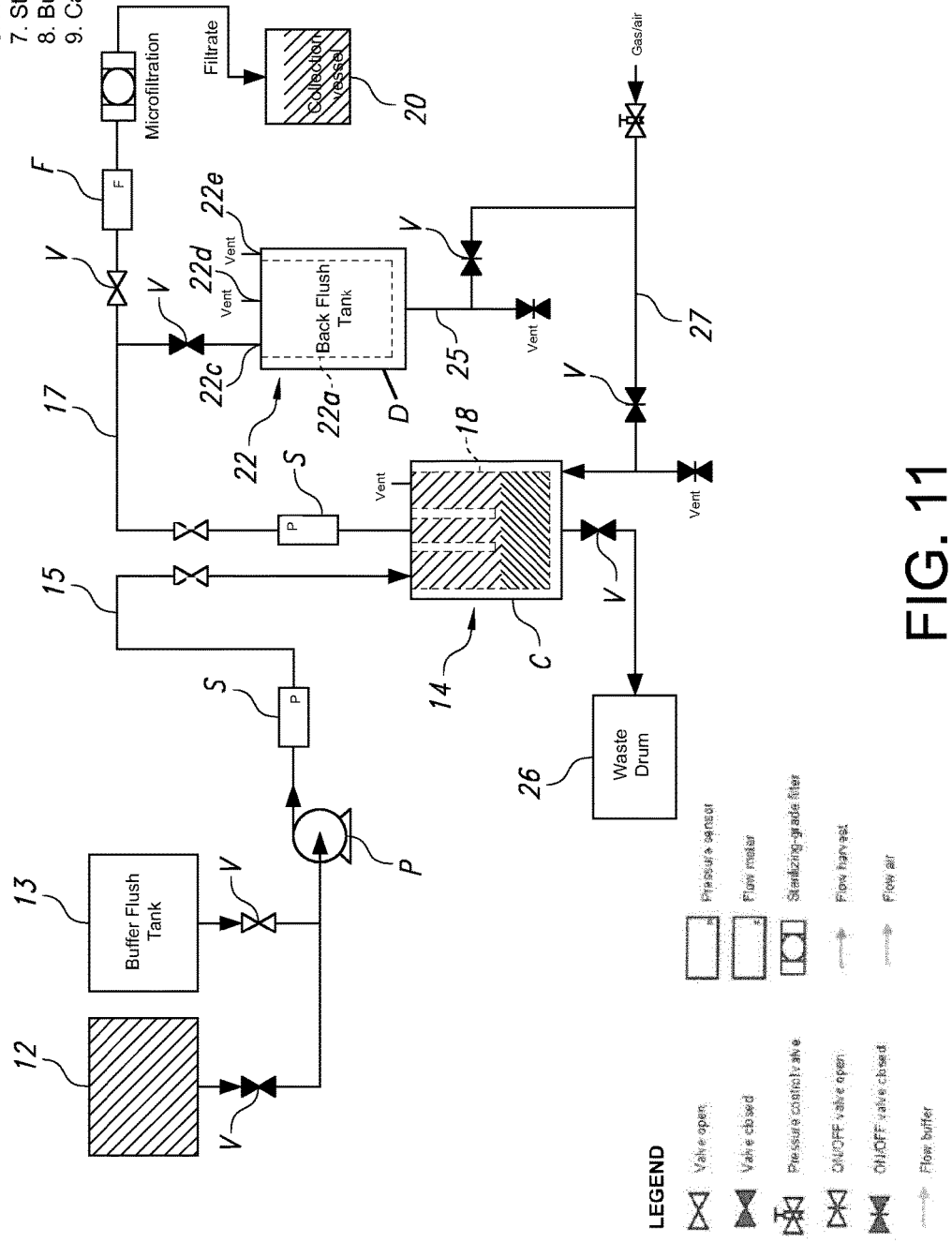

The above-described steps create a single cycle, which may of course be repeated as necessary or desired (see FIGS. 10-13). Specifically, FIG. 11 illustrates the delivery of buffer from source 13 to the filtration vessel 14, which may be done to wash the dynamic filter media 30 and then filter the liquid using the above-described squeezing technique, as indicated in FIG. 12. Buffer may also be delivered to the backflush vessel 22 for use during a subsequent cycle. Once the clarifying is completed, waste may be discharged from the bag 18 via the drain 14c (such as by opening a valve V), which may lead to a waste vessel 26 or drum, as indicated in FIG. 13.

FIG. 14 is a flow chart illustrating the above steps (some optional, such as heel filtration, second heel filtration, or buffer chase) for a method 100 of achieving clarification, but references an initial step 102 of providing a cell culture harvest solution. This may be done using an upstream bioreactor 12 as the feed source (or an intermediate vessel downstream of the bioreactor). The delivery rate may be arranged so as to correspond to the emptying of filtrate from the filtration vessel 14 and the release of the cake from the filter 16. The steps as noted above may be performed, including: (1) step 104, delivering feed to the filtration vessel 14; (2) step 106, filtration into the backflush vessel 22; (3) step 108, filtration from the filtration vessel 14 to the collection vessel 20; (4) step 110, "heel" filtration (squeezing bag 18); (4) step 112, backflushing to release the cake from candle filter(s) 16; and (5) step 114, a second "heel" filtration. This cycle may then be repeated, as necessary or until the filtration vessel 14 accumulates sufficient dynamic media such that a buffer "chase," step 116, is introduced, and the "cake" (dynamic filter media) is discharged as waste, step 118. This chart also indicates that the clarified filtrate of collection vessel 20 at step 108 may be delivered to a further downstream filtering process, step 120, including further filtration and polishing, which may be used to recover the target molecules of interest from the filtrate. As can be understood, the above-described efficient and economical clarification process may reduce the need for further downstream filtration steps, and thus enhance the overall process from generation of the cell culture harvest solution to recovery of a final product of interest.

The system 10 and method described may be provided with one or more single use components. For instance, the filtration vessel 14 may be made disposable (or, alternatively, just the liner or bag 18), and the same can be done for the backflush vessel 22 (including for bag 22a). As can be appreciated, the use of disposable components, and bags 18, 22a in particular, reduces the operating costs, and avoids the need for cleaning and associated validation. The vessels 14 and 22 may also be made to operate under sterile conditions, and the ability to regenerate the dynamic filter media 30 through multiple cycles allows for a continuous process to be realized that maintains sterility (as compared to the need to change or clean a filter during each clarification cycle for a typical cell harvest solution).

Example

As one example of a filtration vessel 14:
Internal diameter 11 cm;
Outside diameter 12 cm;
Working volume height: 19 cm;
Overall height including the support: 24 cm;
As one example of a back-flush vessel 22:
ID=11 cm;
OD=12 cm;
Working volume height=15 cm;
Overall height=16 cm.

This arrangement is sufficient to clarify 8 to 12 L of harvest without performing the cake discharge.

With cake discharge the same filtration vessel 14 would allow to clarify 100 L with 10 cycles. This system integrates intensification technologies, thereby drastically reducing the size of each compartment and hence creating a low footprint production and purification system. The production and purification of the biomolecule can be performed as a continuous and automated process based on this system: from cell culture to final product purification minimizing human intervention. The process intensification and integration enable the containment of all compartments into an isolator ensuring the safety of process operators and the environment. The system has a small footprint. In some embodiments, the footprint of the system is less than about 50 m2, 40 m2, 30 m2, 20 m2, 10 m2, 5 m2, or less. In some embodiments, the footprint of the system is from about 5 m2 to 10 m2, 5 m2 to 20 m2, 5 to 30 m2, 5 to 40 m2 5 to 50 m2. In an example, the footprint is less than 10 m2.

As used herein, the following terms have the following meanings:

"A", "an", and "the" as used herein refers to both singular and plural unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise," "comprising," and "comprises" and "comprised of" as used herein are synonymous with "include", "including", "includes" or "contain", "containing", "contains" and are inclusive or open-ended terms that specifies the presence of what follows, e.g. component, and do not exclude or preclude the presence of additional, non-recited components, features, element, members, steps, known in the art or disclosed therein.

The recitation of numerical ranges by endpoints includes all numbers and fractions subsumed within that range, as well as the recited endpoints.

The terms "Cell culture harvest", "culture harvest" and "harvest" are used herein as synonyms and refer to the unclarified cell culture obtained at the end of culturing cells in a bioreactor. The cultured cells or the grown cells also are referred to as host cells.

The term "bioreactor" as used herein refers to any device or system that supports a biologically active environment, for example for cultivation of cells or organisms for production of a biological product. This would include cell stacks, roller bottles, shakes, flasks, stirred tank suspension bioreactors, high cell density fixed bed perfusion bioreactors, etc.

The diatomaceous earth used in the method or system according to the disclosure can be of various grades, wherein the grade gives an indication of the size of the pores present in the diatomaceous earth. The grade of diatomaceous earth used in a method or system according to the disclosure depends on the morphology, particularly when used in cell culture purification, the size and the shape, of the cells from which a clarified cell culture is to be obtained. For example, for CHO cell cultures, Celpure 300® grade or Celpure 100® grade can be used. For CHO cell cultures grown in an adherent environment such as with a high cell density fixed bed bioreactor, Cellpure 100® grade or Celpure 65® grade can be used. The smaller the floccules, the finer the grade of DE needed, in general.

The term "filtration" or "separation" refers to the removal of the aqueous phase, containing the soluble molecules of interest, from insoluble particles.

The term "target molecule" refers to an organic molecule in a living organism, having characteristics typical of molecules found in or secreted by living organisms including individual cells and that may be naturally occurring or may be artificial (not found in nature and not identical to a molecule found in nature). Example target biomolecules include but are not limited to proteins, peptides, amino acids, glycoproteins, nucleic acids, nucleotides, nucleosides, oligonucleotides, sugars, oligosaccharides, lipids, hormones, proteoglycans, carbohydrates, polypeptides, polynucleotides, polysaccharides.

The foregoing has been presented for purposes of illustration and description. It is not intended to be exhaustive or to limit the embodiments to the precise form disclosed. Obvious modifications and variations are possible in light of the above teachings. All such modifications and variations are within the scope of the appended claims when interpreted in accordance with the breadth to which they are fairly, legally and equitably entitled.

What is claimed:

1. A system for clarifying a cell culture harvest solution, including target molecules and dynamic filter media, comprising:
    a filtration vessel comprising an outer container which is rigid or semi-rigid, a flexible liner contained in the outer container, and an outlet;

the filtration vessel including at least one filter located within the flexible liner, each filter having a lateral side surface, a pump or actuator adapted to create a pressure differential which generates a flow perpendicular to the lateral side surface of each filter and causes the dynamic filter media to accumulate into a cake on the lateral side surface of each filter, said cake and at least one filter adapted, during filtration operation, to permit a filtrate including the target molecules to pass therethrough and said cake, during filtration operation, adapted to prevent unwanted solid materials from passing therethrough; and a backflush source including a backflush fluid and fluidly connected to the filtration vessel via the at least one filter, said backflush source, during backflush operation, adapted to supply backflush fluid back through the at least one filter and cake accumulated on the lateral side surface of each filter, for removing the cake formed on the at least one filter, wherein the cake removed from the at least one filter is discharged through the outlet in the filtration vessel.

2. The system of claim 1 wherein the backflush source is a backflush vessel adapted for receiving a portion of the filtrate from the filtration vessel.

3. The system of claim 1 further including a bioreactor vessel or intermediate vessel within which the cell culture harvest solution and dynamic filter media is mixed and capable of supplying the cell culture harvest solution to the filtration vessel.

4. The system of claim 1, further including a source of the dynamic filter media for being combined with the cell culture harvest solution after delivery from a bioreactor or intermediate vessel.

5. The system of claim 1 further including a bioreactor vessel for supplying the cell culture harvest solution to the filtration vessel and an auxiliary vessel for supplying the dynamic filtration media.

6. The system of claim 1, including the actuator for causing the flexible liner to collapse and causing liquid therein to pass through the at least one filter.

7. The system of claim 6, wherein the actuator comprises a source of pressurized fluid.

8. The system of claim 1, wherein the at least one filter is suspended within the filtration vessel.

9. The system of claim 1, further including a waste collector in fluid communication with the outlet of the filtration vessel for receiving waste including the cake therefrom.

10. The system of claim 1, further including a source of buffer in communication with the filtration vessel.

11. The system of claim 1, including the pump for pumping liquid to the filtration vessel.

12. The system of claim 1, further including a plurality of filters in the filtration vessel.

13. The system of claim 1, wherein the backflush source includes a collapsible liner, and further including the actuator for causing the collapsible liner to collapse and cause fluid therein to pass through the at least one filter and into the flexible liner or outer container of the filtration vessel.

14. The system of claim 1, wherein the filtration vessel further includes a valve for selectively allowing for the draining of fluid through the outlet.

15. The system of claim 14, wherein the valve is located adjacent to a bottom portion of the vessel.

16. The system of claim 1 including a manifold adapted to connect with a source of cell culture harvest solution containing target molecules, the dynamic filter media, and the filtration vessel.

17. A microfacility including the system of claim 1.

* * * * *